(12) United States Patent
Tatake et al.

(10) Patent No.: US 7,829,664 B2
(45) Date of Patent: Nov. 9, 2010

(54) MODIFIED NUCLEOTIDE SEQUENCE ENCODING GLUCAGON-LIKE PEPTIDE-1 (GLP-1), NUCLEIC ACID CONSTRUCT COMPRISING SAME FOR PRODUCTION OF GLUCAGON-LIKE PEPTIDE-1 (GLP-1), HUMAN CELLS COMPRISING SAID CONSTRUCT AND INSULIN-PRODUCING CONSTRUCTS, AND METHODS OF USE THEREOF

(75) Inventors: Revati J. Tatake, Sandy Hook, CT (US); Margaret M. O'Neill, Danbury, CT (US); Kelli-Ann Monaco, New Milford, CT (US)

(73) Assignee: Boehringer Ingelheim International GmbH (DE)

( * ) Notice: Subject to any disclaimer, the term of this patent is extended or adjusted under 35 U.S.C. 154(b) by 201 days.

(21) Appl. No.: 11/756,821

(22) Filed: Jun. 1, 2007

(65) Prior Publication Data
US 2008/0299096 A1  Dec. 4, 2008

(51) Int. Cl.
*A61K 38/22* (2006.01)
*A61K 31/711* (2006.01)
*A61K 48/00* (2006.01)
*C12N 15/00* (2006.01)
*C12N 15/17* (2006.01)

(52) U.S. Cl. .................... 530/303; 424/93.1; 424/93.21; 435/69.4; 435/69.7; 435/71.1; 435/320.1; 514/2; 514/44 R; 530/324; 530/399; 536/23.1; 536/23.51

(58) Field of Classification Search ............... 424/93.1, 424/93.21; 435/69.4, 69.7, 71.1, 320.1; 514/2, 514/44 R; 530/303, 324, 399; 536/23.1, 536/23.51
See application file for complete search history.

(56) References Cited
FOREIGN PATENT DOCUMENTS

WO  WO0136643 A1  5/2001
WO  WO03014318 A2  2/2003
WO  WO03030946 A1  4/2003

OTHER PUBLICATIONS

Sures et al, Science 208(4439):57-59, 1980.*
International Search Report and Written Opinion of the International Application No. PCT/US2008/065015.
M. Kumar, Y. Hunag, Y. Glinka, GJ Prud'Homme, Q. Wang, Gene therapy of diabetes Using a novel GLP-1/lgG1-Fc fusion construct normalizes glucose levels in db/db mice, Gene Therapy (2007) 14, 162-172 XP-002499114.
GB Parsons, DW Souza, H. Wu, D. Yu, SG Wadsworth, RJ Gregory, D. Armentano, Ectopic expression of glucagon-like peptide 1 gene therapy of type II diabetes, Gene Therapy (2007) 14, 38-48 XP-002499115.

* cited by examiner

Primary Examiner—Kevin K. Hill
(74) Attorney, Agent, or Firm—Michael P. Morris; Edouard G. Lebel; Mary-Ellen M. Devlin

(57) ABSTRACT

An isolated chimeric GLP-1 nucleic acid sequence encoding a human pro-insulin leader, a glucagon-like peptide-1 (GLP-1), and a furin cleavable site between the human pro-insulin leader sequence and the GLP-1 is provided. Also provided is an isolated modified chimeric GLP-1 nucleic acid sequence encoding a human pro-insulin leader, a glucagon-like peptide-1 (GLP-1), and a furin cleavable site between the human pro-insulin leader sequence and the GLP-1. Recombinant expression vectors comprising the chimeric GLP-1 nucleic acid sequences, which produce GLP-1 constitutively are provided, as are human cells transfected with such an expression vector in combination with an expression vector comprising a proinsulin nucleic acid sequence and an expression vector comprising a furin and a glucose-regulatable TGF-alpha promoter. Methods of producing human GLP-1 constitutively are provided as are method of producing GLP-1 and insulin or in a glucose-dependent manner using such transfected cells. Methods of treating a subject having Type II diabetes and methods of treating a subject prone to hyperglycemia or suffering from hyperglycemia are provided in which transfected cells produce human GLP-1 and insulin in a glucose-dependent manner. Also provided are methods of reducing weight in a subject by implanting into the subject transfected cells which produce human GLP-1 and insulin in a glucose-dependent manner.

11 Claims, 15 Drawing Sheets

Active GLP-1 Peptide

7                                                             37

<u>H</u>AEGT F<u>TSD</u>V SSYLE GQAAK EF<u>IA</u>W LVKGR G

Underscored residues are critical for GLP-1 action

Sequence Alignment of Native and Optimized GLP-1

```
                                    0.2     0.2 0.4                                    0.2 0.4
(1)   GCG GAA TTC GCC ACC ATG GCC CTC TGG ATG AGA CTG CCC CTG CTG GCC
(1)   --- GAA TTC GCC CTG TGG ATG CGC CTG CCC CTG CTG GCG
                           0.4                         0.19 0.2              0.4  0.11
       A    E    F    A    T    M    A    L    W    M    R    L    P    L    L    A 0.33 0.46  0.28
(51)  CTG CTG GCC CTC TGG GGA CCC GAT CCT GCC GCC --- --- TTG CTA GCC ACC ATG
(36)  CTG CTG GCG CTC TGG GGA CCT GAC CCA GCA GCC GCA GCC TTG GTA GCC CTG ACC ATG
            0.2                0.28    0.54 0.27
       L    L    A    L    W    G    P    D    P    A    A    A    L    V    A    L    T    M 0.2      0.59 0.4 0.58 0.34           0.55         0.24 0.46    0.24
(88)  --- AGA CAG AAG AGA CAC GAC GAG TTC GAG CGC CAC GCC GAG GGA ACC TTC ACC AGC GAC GTA AGC
(86)  GGG CGG CAG AAG CGT CAT GAT GAA TTT GAA CGT CAT GCT GAA GGG ACC TTT ACC AGT GAT GTA AGT
                 0.21  0.08 0.41 0.26 0.42 0.25                    0.45  0.15 0.54  0.15
       G    R    Q    K    R    H    A    E    F    E    R    H    A    E    G    T    F    T    S    D    V    S 0.24                        0.25 0.74 0.4      0.26                      0.48              0.15 0.11
(133) AGC TAT CTG GAG GGC CAG GCC GCT AAG GAG TTC ATC GCT TGG CTT GTA AAA
(136) TCT TAT CTC GAG GGC CAA GCC AAG GAG TTC ATT GCT TGG CTG GTG AAA
              0.18  0.34 0.26 0.26 0.4              0.42  0.4                   0.35              0.4   0.47
       S    Y    L    E    G    Q    A    A    K    E    F    I    A    W    L    V    K 0.25 0.2    0.5
(183) GGA AGA GGA TGA AAGCTTGC
(186) GGC CGA GGA TAG --------
      0.34 0.11    0.2
       G    R    G
```

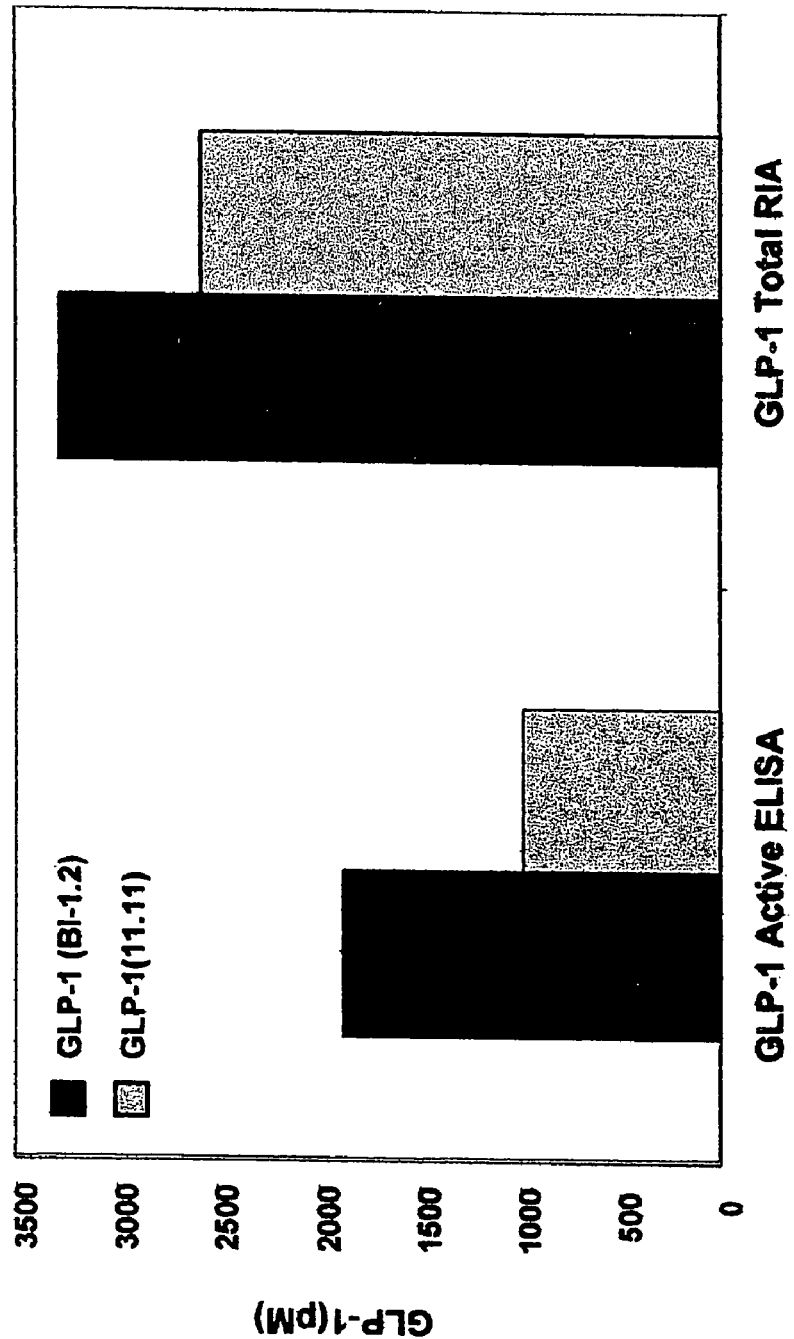

SEQUENCE LISTING

```
<160> NUMBER OF SEQ ID NOS: 25

<210> SEQ ID NO 1
<211> LENGTH: 67
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(67)
<223> OTHER INFORMATION: GLP-1 N-terminal (Sense) Oligonucleotide

<400> SEQUENCE: 1
ctagccacca tggggcggca gaagcgtcat gctgaaggga cctttaccag tgatgtaagt      60
tcttata                                                               67

<210> SEQ ID NO 2
<211> LENGTH: 67
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(67)
<223> OTHER INFORMATION: GLP-1 N-terminus (Anti-sense) oligonucleotide

<400> SEQUENCE: 2
tcgagataag aacttagatc actggtaaag gtcccttcag catgacgctt ctgccgcccc      60
atggtgg                                                               67

<210> SEQ ID NO 3
<211> LENGTH: 56
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
<222> LOCATION: (1)..(56)
<223> OTHER INFORMATION: GLP-1 C-terminus (sense) oligonucleotide

<400> SEQUENCE: 3
tcgagggcca agctgccaag gaattcattg cttggctggt gaaaggccga ggatag          56

<210> SEQ ID NO 4
<211> LENGTH: 56
<212> TYPE: DNA
<213> ORGANISM: Artificial Sequence
<220> FEATURE:
<223> OTHER INFORMATION: Chemically Synthesized
<220> FEATURE:
<221> NAME/KEY: Primer
```

```
<222> LOCATION: (1)..(56)
<223> OTHER INFORMATION: GLP-1 C-terminus (anti-sense) oligonucleotide

<400> SEQUENCE: 4
gatcctatcc tcggcctttc accagccaag caatgaattc cttggcagct tggccc      56

<210> SEQ ID NO 5
<211> LENGTH: 65
<212> TYPE: PRT
<213> ORGANISM: Homo sapiens
<220> FEATURE:
<221> NAME/KEY: Chimera
<222> LOCATION: (1)..(65)
<223> OTHER INFORMATION: Chimeric GLP-1-modified (Human proinsulin
      leader-furin cleavage site-GLP-1)

<400> SEQUENCE: 5

Met Ala Leu Trp Met Arg Leu Leu Pro Leu Leu Ala Leu Leu Ala Leu
1               5                   10                  15

Trp Gly Pro Asp Pro Ala Ala Ala Leu Leu Ala Thr Met Gly Arg Gln
            20                  25                  30

Lys Arg His Ala Glu Gly Thr Phe Thr Ser Asp Val Ser Ser Tyr Leu
        35                  40                  45

Glu Gly Gln Ala Ala Lys Glu Phe Ile Ala Trp Leu Val Lys Gly Arg
    50                  55                  60

Gly
65

<210> SEQ ID NO 6
<211> LENGTH: 198
<212> TYPE: DNA
<213> ORGANISM: Homo sapiens
<220> FEATURE:
<221> NAME/KEY: Chimera
<222> LOCATION: (1)..(198)
<223> OTHER INFORMATION: Chimeric GLP-1-native (Human proinsulin
      leader-furin cleavage site-GLP-1)

<400> SEQUENCE: 6
atggccctgt ggatgcgcct cctgcccctg ctggcgctgc tggccctctg ggacctgac     60 ccagccgcag ccttgctagc caccatgggg cggcagaagc gtcatgctga agggaccttt   120
accagtgatg taagttctta tctcgagggc caagctgcca ggaattcat tgcttggctg    180 gtgaaaggcc gaggatag                                                  198

<210> SEQ ID NO 7
<211> LENGTH: 59
<212> TYPE: PRT
<213> ORGANISM: Homo sapiens
<220> FEATURE:
<221> NAME/KEY: Chimera
<222> LOCATION: (1)..(59)
<223> OTHER INFORMATION: Chimeric GLP-1-modified (Human proinsulin
      leader-furin cleavage site-GLP-1)

<400> SEQUENCE: 7

Met Ala Leu Trp Met Arg Leu Leu Pro Leu Leu Ala Leu Leu Ala Leu
1               5                   10                  15

Trp Gly Pro Asp Pro Ala Ala Ala Arg Gln Lys Arg His Ala Glu Gly
            20                  25                  30

Thr Phe Thr Ser Asp Val Ser Ser Tyr Leu Glu Gly Gln Ala Ala Lys
        35                  40                  45

Glu Phe Ile Ala Trp Leu Val Lys Gly Arg Gly
    50                  55
```

<210> SEQ ID NO 8
<211> LENGTH: 180
<212> TYPE: DNA
<213> ORGANISM: Homo sapiens
<220> FEATURE:
<221> NAME/KEY: Chimera
<222> LOCATION: (1)..(180)
<223> OTHER INFORMATION: Chimeric GLP-1-modified (Human proinsulin
      leader-furin cleavage site-GLP-1)

<400> SEQUENCE: 8
atggccctct ggatgagact gctgccctg ctcgccctgc tcgccctgtg gggacccgat      60
cctgccgccg ccagacagaa gagacacgcc gagggcacct tcaccagcga cgtaagcagc    120
tatctggagg acaggccgc taaggagttc atcgcttggc ttgtaaaagg aagaggatga    180

<210> SEQ ID NO 9
<211> LENGTH: 31
<212> TYPE: PRT
<213> ORGANISM: Homo sapiens
<220> FEATURE:
<221> NAME/KEY: GLP-1
<222> LOCATION: (1)..(31)
<223> OTHER INFORMATION: GLP (7-37)

<400> SEQUENCE: 9

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 10
<211> LENGTH: 30
<212> TYPE: PRT
<213> ORGANISM: Homo sapiens
<220> FEATURE:
<221> NAME/KEY: GLP-1
<222> LOCATION: (1)..(30)
<223> OTHER INFORMATION: GLP-1 (7-36)

<400> SEQUENCE: 10

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 11
<211> LENGTH: 96
<212> TYPE: DNA
<213> ORGANISM: Homo sapiens
<220> FEATURE:
<221> NAME/KEY: GLP-1
<222> LOCATION: (1)..(96)
<223> OTHER INFORMATION: GLP-1 modified

<400> SEQUENCE: 11
cacgccgagg gcaccttcac cagcgacgta agcagctatc tggagggaca ggccgctaag    60
gagttcatcg cttggcttgt aaaaggaaga ggatga                              96

<210> SEQ ID NO 12
<211> LENGTH: 39
<212> TYPE: PRT
<213> ORGANISM: Artificial Sequence
<220> FEATURE:

-continued

```
<223> OTHER INFORMATION: Chemically Synthesized
<220> FEATURE:
<221> NAME/KEY: Exenatide
<222> LOCATION: (1)..(39)
<223> OTHER INFORMATION: Exenatide is a synthetic version of exendin-4,
      a naturally occuring hormone

<400> SEQUENCE: 12

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 13
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 13

Leu Leu Ala Thr Met Gly
1               5

<210> SEQ ID NO 14
<211> LENGTH: 13
<212> TYPE: RNA
<213> ORGANISM: Artificial Sequence
<220> FEATURE:
<223> OTHER INFORMATION: Chemically Synthesized
<220> FEATURE:
<221> NAME/KEY: Kozak
<222> LOCATION: (1)..(13)
<223> OTHER INFORMATION: Consensus sequence for translation initiation
      in vertebrates
<300> PUBLICATION INFORMATION:
<301> AUTHORS: Kozak
<302> TITLE: Point mutations define a sequence flanking the AUG
      initiator codon that modulates translation by eukaryotic
      ribosomes.
<303> JOURNAL: Cell
<304> VOLUME: 44
<305> ISSUE: 2
<306> PAGES: 283-292
<307> DATE: 1986-01-31

<400> SEQUENCE: 14
gccgccacca ugg                                                          13

<210> SEQ ID NO 15
<211> LENGTH: 24
<212> TYPE: PRT
<213> ORGANISM: Homo sapiens
<220> FEATURE:
<221> NAME/KEY: SIGNAL
<222> LOCATION: (1)..(24)
<223> OTHER INFORMATION: preproinsulin signal sequence

<400> SEQUENCE: 15

Met Ala Leu Trp Met Arg Leu Leu Pro Leu Leu Ala Leu Leu Ala Leu
1               5                   10                  15

Trp Gly Pro Asp Pro Ala Ala Ala
            20

<210> SEQ ID NO 16
<211> LENGTH: 4
```

```
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (2)..(3)
<223> OTHER INFORMATION: furin cleavage site where Xaa is any one of the
      twenty amino acids, preferably Lys or Arg

<400> SEQUENCE: 16

Arg Xaa Xaa Arg
1

<210> SEQ ID NO 17
<211> LENGTH: 4
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (2)..(2)
<223> OTHER INFORMATION: furin cleavage site where Xaa is any one of the
      twenty amino acids, preferably Lys or Arg

<400> SEQUENCE: 17

Arg Xaa Arg Arg
1

<210> SEQ ID NO 18
<211> LENGTH: 4
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (2)..(2)
<223> OTHER INFORMATION: furin cleavage site where Xaa is any one of the
      twenty amino acids, preferably Lys or Arg

<400> SEQUENCE: 18

Arg Xaa Lys Arg
1

<210> SEQ ID NO 19
<211> LENGTH: 4
<212> TYPE: PRT
<213> ORGANISM: Artificial Sequence
<220> FEATURE:
<223> OTHER INFORMATION: Chemically Synthesized
<220> FEATURE:
<221> NAME/KEY: SITE
<222> LOCATION: (1)..(4)
<223> OTHER INFORMATION: furin cleavage site

<400> SEQUENCE: 19

Arg Gln Lys Arg
1

<210> SEQ ID NO 20
<211> LENGTH: 198
<212> TYPE: DNA
<213> ORGANISM: Homo sapiens
<220> FEATURE:
<221> NAME/KEY: Chimera
<222> LOCATION: (1)..(198)
<223> OTHER INFORMATION: Chimeric GLP-1-native (Human proinsulin
      leader-furin cleavage site-GLP-1)
<220> FEATURE:
```

```
<221> NAME/KEY: misc_feature
<222> LOCATION: (73)..(90)
<223> OTHER INFORMATION: n is any nucleotide (a, c, g or t)

<400> SEQUENCE: 20
atggccctgt ggatgcgcct cctgcccctg ctggcgctgc tggccctctg gggacctgac    60
ccagccgcag ccnnnnnnnn nnnnnnnnnn cggcagaagc gtcatgctga agggaccttt   120
accagtgatg taagttctta tctcgagggc caagctgcca aggaattcat tgcttggctg   180
gtgaaaggcc gaggatag                                                 198

<210> SEQ ID NO 21
<211> LENGTH: 65
<212> TYPE: PRT
<213> ORGANISM: Homo sapiens
<220> FEATURE:
<221> NAME/KEY: Chimera
<222> LOCATION: (1)..(65)
<223> OTHER INFORMATION: Chimeric GLP-1-modified (Human proinsulin
      leader-furin cleavage site-GLP-1)
<220> FEATURE:
<221> NAME/KEY: MISC_FEATURE
<222> LOCATION: (25)..(30)
<223> OTHER INFORMATION: Xaa is any one of the twenty amino acids

<400> SEQUENCE: 21

Met Ala Leu Trp Met Arg Leu Leu Pro Leu Leu Ala Leu Leu Ala Leu
1               5                  10                  15

Trp Gly Pro Asp Pro Ala Ala Ala Xaa Xaa Xaa Xaa Xaa Xaa Arg Gln
            20                  25                  30

Lys Arg His Ala Glu Gly Thr Phe Thr Ser Asp Val Ser Ser Tyr Leu
        35                  40                  45

Glu Gly Gln Ala Ala Lys Glu Phe Ile Ala Trp Leu Val Lys Gly Arg
    50                  55                  60

Gly
65

<210> SEQ ID NO 22
<211> LENGTH: 198
<212> TYPE: DNA
<213> ORGANISM: Homo sapiens
<220> FEATURE:
<221> NAME/KEY: Chimera
<222> LOCATION: (1)..(198)
<223> OTHER INFORMATION: Chimeric GLP-1-native (Human proinsulin
      leader-furin cleavage site-GLP-1)
<220> FEATURE:
<221> NAME/KEY: misc_feature
<222> LOCATION: (75)..(90)
<223> OTHER INFORMATION: n is any nucleotide (a, c, g or t)

<400> SEQUENCE: 22
atggccctgt ggatgcgcct cctgcccctg ctggcgctgc tggccctctg gggacctgac    60
ccagccgcag ccgcngcngc ngcngcngcn cggcagaagc gtcatgctga agggaccttt   120
accagtgatg taagttctta tctcgagggc caagctgcca aggaattcat tgcttggctg   180
gtgaaaggcc gaggatag                                                 198

<210> SEQ ID NO 23
<211> LENGTH: 65
<212> TYPE: PRT
<213> ORGANISM: Homo sapiens
<220> FEATURE:
<221> NAME/KEY: Chimera
<222> LOCATION: (1)..(65)
```

```
<223> OTHER INFORMATION: Chimeric GLP-1-modified (Human proinsulin
      leader-furin cleavage site-GLP-1)

<400> SEQUENCE: 23

Met Ala Leu Trp Met Arg Leu Leu Pro Leu Leu Ala Leu Leu Ala Leu
1               5                   10                  15

Trp Gly Pro Asp Pro Ala Ala Ala Ala Ala Ala Ala Ala Arg Gln
            20                  25                  30

Lys Arg His Ala Glu Gly Thr Phe Thr Ser Asp Val Ser Ser Tyr Leu
            35                  40                  45

Glu Gly Gln Ala Ala Lys Glu Phe Ile Ala Trp Leu Val Lys Gly Arg
    50                  55                  60

Gly
65

<210> SEQ ID NO 24
<211> LENGTH: 210
<212> TYPE: DNA
<213> ORGANISM: Homo sapiens
<220> FEATURE:
<221> NAME/KEY: Chimera
<222> LOCATION: (13)..(210)
<223> OTHER INFORMATION: Chimeric GLP-1-native (Human proinsulin
      leader-furin cleavage site-GLP-1)

<400> SEQUENCE: 24
gaattcctgg ccatggccct gtggatgcgc ctcctgcccc tgctggcgct gctggccctc      60
tggggacctg acccagccgc agccttgcta gccaccatgg ggcggcagaa gcgtcatgct     120
gaagggacct ttaccagtga tgtaagttct tatctcgagg ccaagctgc caaggaattc      180 attgcttggc tggtgaaagg ccgaggatag                                       210

<210> SEQ ID NO 25
<211> LENGTH: 203
<212> TYPE: DNA
<213> ORGANISM: Homo sapiens
<220> FEATURE:
<221> NAME/KEY: Chimera
<222> LOCATION: (16)..(195)
<223> OTHER INFORMATION: Chimeric GLP-1-modified (Human proinsulin
      leader-furin cleavage site-GLP-1)

<400> SEQUENCE: 25
gcggaattcg ccaccatggc cctctggatg agactgctgc cctgctcgc cctgctcgcc       60 ctgtggggac ccgatcctgc cgccgccaga cagaagagac acgccgaggg caccttcacc     120
agcgacgtaa gcagctatct ggagggacag gccgctaagg agttcatcgc ttggcttgta     180
aaaggaagag gatgaaagct tgc                                              203
```

MODIFIED NUCLEOTIDE SEQUENCE ENCODING GLUCAGON-LIKE PEPTIDE-1 (GLP-1), NUCLEIC ACID CONSTRUCT COMPRISING SAME FOR PRODUCTION OF GLUCAGON-LIKE PEPTIDE-1 (GLP-1), HUMAN CELLS COMPRISING SAID CONSTRUCT AND INSULIN-PRODUCING CONSTRUCTS, AND METHODS OF USE THEREOF

BACKGROUND OF THE INVENTION

The present invention relates to nucleic acid constructs encoding human GLP-1 peptide and human cells engineered for expression of these nucleic acid constructs to produce GLP-1 peptide and insulin for the treatment and prevention of diabetes, hyperglycemia and weight reduction. The nucleic acid constructs comprise a natural or modified nucleotide sequence which encodes natural human glucagon-like peptide-1 (GLP-1). The modified construct was made using optimized codon usage (Codon Usage Database is available at www.kazusa.or.jp/codon/) and nucleic acid fragment was synthesized commercially (Aptagen, Inc). Preferably, the constructs comprise natural or modified chimeric nucleic acid sequence encoding a human pro-insulin leader, a glucagon-like peptide-1 (GLP-1), and a furin cleavable site between the human pro-insulin leader sequence and the GLP-1. Engineered human cell lines comprising these constructs and which produce natural GLP-1 constitutively by utilizing endogenously produced furin are provided. The engineered cells which produce GLP-1 constitutively may also have a nucleic acid construct encoding furin, which is expressed in a glucose-regulated manner. Also provided are engineered human cells expressing both GLP-1 and proinsulin constitutively and expressing furin in a glucose-dependent manner, wherein the proinsulin and GLP-1 nucleic acid sequences each also encode a furin cleavable site, such that upon furin expression in a glucose-regulated manner, i.e., in the presence of an elevated blood glucose level, cleavage of the proinsulin and GLP-1 chimeric sequences by furin at the respective furin cleavage sites produces insulin and GLP-1. Both types of engineered cells, i.e., the constitutively producing GLP-1 cells; and cells co-producing GLP-1 and insulin constitutively and furin in a glucose-dependent manner, may be used for the treatment and prevention of diabetes, hyperglycemia and weight reduction.

Diabetes mellitus is a group of diseases characterized by high levels of blood glucose. Type I diabetes, previously called insulin-dependent diabetes mellitus (IDDM) or juvenile-onset diabetes, occurs when the immune system destroys pancreatic beta cells, the cells which make the hormone insulin that regulates blood sugar. Type II diabetes, previously called non-insulin dependent diabetes mellitus (NIDDM) or adult-onset diabetes, begins as insulin resistance, i.e., increased hepatic glucose production and decreased insulin-mediated glucose transport at the muscle and adipose tissue level; as the need for insulin rises, the pancreas gradually loses its ability to produce insulin. About 90% to 95% of all diagnosed cases of diabetes are Type II diabetes. This type of diabetes is associated with older age, obesity, family history of diabetes, history of gestational diabetes, impaired glucose metabolism, physical inactivity, and race/ethnicity. Gestational diabetes is characterized by glucose intolerance during pregnancy and occurs more frequently among obese women and those with a family history of diabetes; after pregnancy some women who have had gestational diabetes may develop Type II diabetes. Other types of diabetes occur due to genetic conditions or other factors such as drugs, surgery, malnutrition, infections and other diseases.

GLP-1, an insulinotropic hormone, is secreted postprandially by intestinal L cells as a proteolytic cleavage product of pre-pro-glucagon. It is know as an incretin or gut hormone. GLP-1 has pleiotropic biological effects and the clinical implications of which are very important for type II diabetic patients. GLP-1 has been shown to be a transcriptional inducer of islet cell-specific genes. It stimulates insulin secretion by beta cells in response to an increase in glucose levels and is also responsible for inhibition of glucagon secretion and a decrease in the rate of gastric emptying and acid secretion. GLP-1 has been shown to increase islet cell mass by promoting beta cell neogenesis from ductal cells. The role of GLP-1 in glucose tolerance and the possible involvement of this peptide hormone in the pathogenesis of diabetes makes it a candidate as a new therapeutic agent for people with Type II diabetes. In diabetic patients, a significant induction of insulin secretion and correction of post-prandial hyperglycemia has been achieved by injecting pharmacological, i.e., therapeutically effective, levels of GLP-1 (50-100 pM). Intravenous infusion of GLP-1 in fasted Type II diabetic patients, who were markedly hyperglycemic, completely corrected their blood glucose levels. Thus, GLP-1 appears to be a good therapeutic agent to control hyperglycemia in patients who have Type II diabetes. However, its potential as a new therapeutic agent is limited because this peptide cannot be administered orally, and it has short half life (about 5 minutes or less) in vivo.

GLP-1 is a product of posttranslational processing of the glucagon precursor proglucagon in intestinal L cells and the brain. Other peptide hormones derived from proglucagon include glucagon (in the pancreas) and oxyntomodulin and GLP-2 (in the intestines and brain). There are two forms of full length N-terminal GLP-1, GLP-1 (1-37) and GLP-1 (1-36)amide. Both forms are active and are produced when the GLP-1 polypeptide is cleaved to remove the first six amino acids resulting in the active peptides GLP-1 (7-37), having 31 amino acids, and GLP-1 (7-36) amide, having 30 amino acids. The majority of circulating biologically active GLP-1 is found in the amidated form, GLP-1 (7-36) amide, with lesser amounts of the bioactive non-amidated GLP-1 (7-37) also detectable. The active GLP-1 undergoes rapid degradation by N-terminal cleavage of the first two amino acids ($His^1$-$Ala^2$) by circulating di-peptidyl peptidase IV (DPPIV) resulting in the short half life of GLP-1.

On Apr. 29, 2005, the U.S. Food and Drug Administration approved the first incretin mimetic, BYETTA® (exenatide) injection, as an adjunct therapy for Type II diabetes patients who have not achieved adequate control of blood sugar with two common oral diabetes medications, metformin and/or sulfonylurea. BYETTA® is also indicated as a monotherapy for patients with Type II diabetes. BYETTA® exhibits many of the same effects as the human incretin hormone GLP-1, in regulating blood sugar, according to the manufacturer. Exenatide is a synthetic version of exendin-4, a naturally-occurring hormone, which is a 39-amino acid peptide amide having the amino acid sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu -Lys-Asn-Gly-Gly-Pro-Ser-Ser-Gly-Ala-Pro-Pro-Pro-Ser-$NH_2$. Exenatide's amino acid sequence partially overlaps that of the human GLP-1, but has a longer half-life than native GLP-1. Exenatide has been shown to bind and activate the known human GLP-1 receptor in vitro.

Analogs of GLP-1, such as extendin-4 or the mutated GLP-1 containing glycine (Gly) as the second amino acid residue, show potent insulinotropic effects and have a longer half life than GLP-1. However, because these molecules are foreign, they cannot be degraded rapidly in the body as native GLP-1. Consequently, a need exists in the field of hyperglycemia treatment, especially in patients with Type II diabetes as well as those having an overweight condition, for nucleic acid constructs that constitutively express human GLP-1, and engineered cells comprising said constructs, to achieve normoglycemia and wherein the produced GLP-1 is degraded when not needed for stimulating insulin production. Nucleic acid constructs which constitutively express nucleic acid sequences comprising human GLP-1 constitutively express nucleic acid constructs comprising proinsulin; and express furin in a glucose-dependent manner, such that an increased level of glucose stimulates furin production, resulting in cleavage at furin cleavable sites of the respective nucleic acid constructs produces GLP-1 and insulin, would provide an alternative form of hyperglycemia treatment, diabetes and overweight conditions. Engineered cells comprising nucleic acid constructs which co-express human GLP-1 and insulin also would provide another therapeutic route for the aforementioned illnesses and/or metabolic conditions.

SUMMARY OF THE INVENTION

This invention provides an isolated modified chimeric GLP-1 nucleic acid sequence encoding a human pro-insulin leader, a glucagon-like peptide-1 (GLP-1), and a furin cleavable site between the human pro-insulin leader sequence and the GLP-1 sequence. In an embodiment, the modified chimeric nucleic acid sequence is shown in SEQ ID NO:8. This invention also provides an isolated chimeric GLP-1 nucleic acid sequence encoding a human pro-insulin leader, a glucagon-like peptide-1 (GLP-1), and a furin cleavable site between the human pro-insulin leader sequence and the GLP-1 sequence. In an embodiment, the isolated chimeric nucleic acid sequence is shown in SEQ ID NO:6.

The present invention also provides a recombinant expression vector comprising an isolated modified chimeric GLP-1 nucleic acid sequence encoding a human pro-insulin leader, a glucagon-like peptide-1 (GLP-1)(7-37), a furin cleavable site between the human pro-insulin leader and the GLP-1(7-37), and a constitutive promoter, e.g., a CMV promoter, which drives the expression of the modified chimeric GLP-1 nucleic acid sequence constitutively. In an embodiment, the modified chimeric nucleic acid sequence is shown in SEQ ID NO:8. In a further embodiment, the recombinant expression vector may further comprise a nucleotide sequence encoding human furin and a glucose-regulatable promoter, e.g., TGF-alpha promoter, which drives the expression of the nucleotide sequence encoding human furin. In further embodiment, the encoded GLP-1 may be GLP-1(7-36).

Also provided by the present invention are human cells stably transfected with (a) a recombinant expression vector comprising an isolated modified chimeric GLP-1 nucleic acid sequence encoding a human pro-insulin leader, a glucagon-like peptide-1 (GLP-1)(7-37), a furin cleavable site between the human pro-insulin leader and the GLP-1(7-37), and a constitutive promoter, e.g., a CMV promoter, which drives the expression of the modified chimeric GLP-1 nucleic acid sequence constitutively; (b) a second expression vector comprising an isolated nucleic acid sequence encoding human furin and a glucose-regulatable TGF-alpha promoter, wherein said promoter drives expression of the nucleotide sequence encoding human furin in a glucose-regulated manner, and (c) a third expression vector comprising an isolated nucleic acid sequence encoding proinsulin, a furin cleavable site between a human pro-insulin leader sequence and insulin sequence and a constitutive promoter which drives the expression of the nucleic acid sequence encoding proinsulin constitutively. Such a human cell is engineered to express furin in glucose-regulated manner, thereby enabling (a) glucose-responsive cleavage of the co-expressed isolated modified chimeric GLP-1 nucleic acid sequence encoding a human pro-insulin leader, a glucagon-like peptide-1 (GLP-1) (7-37), a furin cleavable site between the human pro-insulin leader and the GLP-1 (7-37) at the furin cleavable site to produce active GLP-1(7-37), as well as (b) co-expression of insulin by the furin cleavage of a proinsulin at the furin cleavable site between the human pro-insulin leader sequence and insulin sequence. Such cells produce GLP-1(7-37) in a glucose-dependent manner and are referred to herein as the "glucose-regulated" or "glucose-dependent" GLP-1 producing cells. The cells are also referred to herein as glucose-regulated GLP-1 and insulin co-producing cells or glucose-dependent GLP-1 and insulin co-producing cells. In an embodiment, the modified chimeric nucleic acid sequence is shown in SEQ ID NO:8. In an alternate embodiment, the encoded GLP-1 may be GLP-1(7-36).

In addition, the present invention provides human cells stably transfected with a recombinant expression vector comprising an isolated modified chimeric GLP-1 nucleic acid sequence encoding a human pro-insulin leader, a glucagon-like peptide-1 (GLP-1)(7-37), a furin cleavable site between the human pro-insulin leader and the GLP-1(7-37), and constitutive promoter, e.g., a CMV promoter. Such cells produce GLP-1 constitutively when endogenously produced furin in the cells cleaves a furin cleavable site and are referred to herein as the constitutive GLP-1 producing cells. In an embodiment, the modified chimeric nucleic acid sequence is shown in SEQ ID NO:8. The encoded GLP-1 may be GLP-1(7-36) in another embodiment.

The present invention also provides a recombinant expression vector comprising an isolated chimeric GLP-1 nucleic acid sequence encoding a human pro-insulin leader, a glucagon-like peptide-1 (GLP-1)(7-37), a furin cleavable site between the human pro-insulin leader and the GLP-1 (7-37), and a constitutive promoter, e.g., a CMV promoter, which drives the expression of the chimeric GLP-1 nucleic acid sequence constitutively. The expression vector may further comprising a nucleotide sequence encoding human furin and a glucose-regulatable promoter, e.g., TGF-alpha promoter, which drives the expression of the nucleotide sequence encoding human furin in a glucose-dependent manner. In this embodiment, GLP-1(7-37) is produced in a glucose-regulated manner when the glucose-regulated furin, expressed in the presence of glucose, said glucose being present in a concentration higher than an ambient glucose concentration in the cell, cleaves the furin cleavable site between the human pro-insulin leader and the GLP-1 (7-3). Alternatively, the encoded GLP-1 may be GLP-1(7-36).

Further provided by the present invention are human cells stably transfected with (a) a recombinant expression vector comprising an isolated chimeric GLP-1 nucleic acid sequence encoding a human pro-insulin leader, a glucagon-like peptide-1 (GLP-1)(7-37), a furin cleavable site between the human pro-insulin leader and the GLP-1(7-37), and a constitutive promoter, e.g., a CMV promoter, which drives the expression of the isolated chimeric GLP-1 nucleic acid sequence constitutively; (b) a second expression vector comprising an isolated nucleic acid sequence encoding human furin and a glucose-regulatable TGF-alpha promoter, wherein said promoter drives expression of the nucleotide sequence encoding human furin in a glucose-regulated manner, and (c) a third expression vector comprising an isolated nucleic acid sequence encoding proinsulin, a furin cleavable site between the human pro-insulin leader sequence and insulin sequence and a constitutive promoter which drives the expression of the nucleic acid sequence encoding proinsulin constitutively. Such a human cell is engineered to express furin in glucose-regulated manner, thereby enabling (a) glucose-responsive cleavage of the co-expressed isolated chimeric GLP-1 nucleic acid sequence encoding the human pro-insulin leader, the glucagon-like peptide-1 (GLP-1)(7-37), the furin cleavable site between the human pro-insulin leader and the GLP-1(7-37) at the furin cleavable site to produce active GLP-1(7-37) as well as (b) co-expression of insulin by the furin cleavage of the proinsulin at the furin cleavable site between the human pro-insulin leader sequence and the insulin sequence. Such cells produce GLP-1 in a glucose-dependent manner and also are referred to herein as the "glucose-regulated" or "glucose-dependent" GLP-1 producing cells. The cells are also referred to herein as glucose-regulated GLP-1 and insulin co-producing cells or glucose-dependent GLP-1 and insulin co-producing cells. In an embodiment, the isolated chimeric nucleic acid sequence is shown in SEQ ID NO:6. In a further embodiment, the encoded GLP-1 is GLP-1(7-36).

In addition, the present invention provides human cells stably transfected with a recombinant expression vector comprising an isolated chimeric GLP-1 nucleic acid sequence encoding a human pro-insulin leader, a glucagon-like peptide-1 (GLP-1)(7-37), a furin cleavable site between the human pro-insulin leader and the GLP-1(7-37), and constitutive promoter, e.g., a CMV promoter. Such cells produce GLP-1(7-37) constitutively when endogenously produced furin in the cells cleaves the a furin cleavable site and also are referred to herein as constitutive GLP-1 producing cells. In an embodiment, the isolated chimeric nucleic acid sequence is shown in SEQ ID NO:6.

In another embodiment, the present invention provides an isolated chimeric nucleic acid which encodes a chimeric peptide whose amino acid sequence is modified from SEQ ID NO:5, wherein the amino acid sequence LLATMG is replaced by amino acid sequence $X_1X_2X_3X_4X_5X_6$, wherein $X_1$, $X_2$, $X_3$, $X_4$, $X_5$ and $X_6$ each are an amino acid selected from the group consisting of A, R, N, D, C, E, Q, G, H, I, L, K, M, F, P, S, T, W, Y and V, respectively, wherein said chimeric nucleotide sequence encodes a human pro-insulin leader, a glucagon-like peptide-1 (GLP-1)(7-37), and a furin cleavable site between the human pro-insulin leader and the GLP-1(7-37), wherein the modified amino acid sequence is shown in SEQ ID NO: 21. The GLP-1 may be GLP-1(7-36) in a further embodiment.

In a further embodiment provided is an isolated chimeric nucleotide sequence whose sequence is shown in SEQ ID NO:6, wherein said chimeric nucleotide sequence encodes a human pro-insulin leader, a glucagon-like peptide-1 (GLP-1) (7-37), and a furin cleavable site between the human pro-insulin leader and the GLP-1(7-37), and wherein nucleotides encoding amino acid sequence LLATMG are replaced by nucleotides selected from the group consisting of $N_1$-$N_{18}$, wherein each N is part of a codon selected from the group consisting of GCA/C/G/T, AAC/T, GAC/T, TGC/T, GAC/T, GAA/G, TTC/T, GGA/C/G/T, CAC/T, ATA/C/T, AAA/G, CTA/C/G/T, TTA/G, ATG, AAC/T, CCA/C/G/T, CAA/G, AGA/G, CGA/C/G/T, AGC/T, TCA/C/G/T, ACA/C/G/T, GTA/C/G/T, TGG, TAA/G, TGA, TAC/T, CAA/G and GAA/G, wherein the modified nucleotide sequence is shown is SEQ ID NO: 20. In another embodiment, the GLP-1 is GLP-1(7-36).

The present invention also provides a recombinant expression vector comprising an isolated chimeric nucleic acid which encodes a chimeric peptide whose amino acid sequence is modified from SEQ ID NO:5, wherein the amino acid sequence LLATMG is replaced by amino acid sequence $X_1X_2X_3X_4X_5X_6$, wherein $X_1$, $X_2$, $X_3$, $X_4$, $X_5$ and $X_6$ each are an amino acid selected from the group consisting of A, R, N, D, C, E, Q, G, H, I, L, K, M, F, P, S, T, W, Y and V, respectively; wherein said chimeric nucleotide sequence encodes a human pro-insulin leader, a glucagon-like peptide-1 (GLP-1)(7-37), and a furin cleavable site between the human pro-insulin leader and the GLP-1(7-37), wherein the modified amino acid wequence is shown in SEQ ID NO: 21. In a further embodiment, the GLP-1 is GLP-1(7-36).

Further provided by the present invention are human cells stably transfected with (a) a recombinant expression vector comprising an isolated chimeric GLP-1 nucleic acid sequence encoding a human pro-insulin leader, a glucagon-like peptide-1 (GLP-1), and a furin cleavable site between the human pro-insulin leader and the GLP-1 encoding a human pro-insulin leader, a glucagon-like peptide-1 (GLP-1)(7-37), a furin cleavable site between the human pro-insulin leader and the GLP-1(7-37), and a constitutive promoter, e.g., a CMV promoter, which drives the expression of the isolated chimeric GLP-1 nucleic acid sequence constitutively, wherein the encoded chimeric amino acid sequence is modified from SEQ ID NO:5, wherein the amino acid sequence LLATMG is replaced by amino acid sequence $X_1X_2X_3X_4X_5X_6$, wherein $X_1$, $X_2$, $X_3$, $X_4$, $X_5$ and $X_6$ each are an amino acid selected from the group consisting of A, R, N, D, C, E, Q, G, H, I, L, K, M, F, P, S, T, W, Y and V, respectively; wherein the modified amino acid sequence is shown in SEQ ID NO: 21; (b) a second expression vector comprising an isolated nucleic acid sequence encoding human furin and a glucose-regulatable TGF-alpha promoter, wherein said promoter drives expression of the nucleotide sequence encoding human furin in a glucose-regulated manner, and (c) a third expression vector comprising an isolated nucleic acid sequence encoding proinsulin, a furin cleavable site between the human pro-insulin leader sequence and insulin sequence and a constitutive promoter which drives the expression of the nucleic acid sequence encoding proinsulin constitutively. The expression vector may further comprising a nucleotide sequence encoding human furin and a glucose-regulatable promoter, e.g., TGF-alpha promoter, which drives the expression of the nucleotide sequence encoding human furin in a glucose-dependent manner. In this embodiment, GLP-1(7-37) is produced in a glucose-regulated manner when the glucose-regulated furin, expressed in the presence of glucose, said glucose being present in a concentration higher than an ambient glucose concentration in the cell, cleaves the furin cleavable site between the human pro-insulin leader and the GLP-1 (7-37). In another embodiment, the GLP-1 is GLP-1 (7-36).

This invention provides a method of producing human GLP-1 constitutively in an isolated human cell by stably transfecting the isolated human cells with (a) a recombinant expression vector comprising an isolated modified chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the nucleic acid sequence encoding GLP-1 constitutively, wherein the modified chimeric nucleic acid sequence is shown in SEQ ID NO:8 or (b) a recombinant expression vector comprising an isolated chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the nucleic acid sequence encoding GLP-1 constitutively, wherein the chimeric nucleic acid sequence is shown in SEQ ID NO:6.

This invention also provides a method of producing human GLP-1 and insulin in a glucose-dependent manner in an isolated human cell, said method comprising: (a) stably transfecting the isolated human cell with (i) a recombinant expression vector comprising an isolated modified chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the nucleic acid sequence encoding GLP-1 constitutively, wherein the modified chimeric nucleic acid sequence is shown in SEQ ID NO:8, (ii) a second expression vector comprising an isolated nucleic acid sequence encoding human furin and a glucose-regulatable TGF-alpha promoter, wherein said promoter drives expression of the nucleotide sequence encoding human furin in a glucose-regulated manner, and (iii) a third expression vector comprising an isolated nucleic acid sequence encoding proinsulin, a furin cleavable site between the human pro-insulin leader sequence and insulin sequence and a constitutive promoter which drives the expression of the nucleic acid sequence encoding proinsulin constitutively; and (b) stimulating said cell with a glucose, wherein the concentration of the glucose is higher than an ambient concentration of glucose.

This invention further provides a method of producing human GLP-1 and insulin in a glucose-dependent manner in an isolated human cell, said method comprising: (a) stably transfecting the isolated human cell with (i) a recombinant expression vector comprising an isolated chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the isolated chimeric nucleic acid sequence constitutively, wherein the chimeric nucleic acid sequence is shown in SEQ ID NO:6, (ii) a second expression vector comprising an isolated nucleic acid sequence encoding human furin and a glucose-regulatable TGF-alpha promoter, wherein said promoter drives expression of the nucleotide sequence encoding human furin in a glucose-regulated manner, and (iii) a third expression vector comprising an isolated nucleic acid sequence encoding proinsulin, said proinsulin comprised of a human pro-insulin leader sequence, an insulin sequence and a furin cleavable site between the human pro-insulin leader sequence and the insulin sequence and a constitutive promoter which drives the expression of the nucleic acid sequence encoding proinsulin constitutively; and (b) stimulating said cell with a glucose, wherein the concentration of the glucose is higher than an ambient concentration of glucose.

In another embodiment of the present invention, there is provided a method of treating a subject having Type II diabetes, said method comprising: implanting into the subject an immunoisolatory device, wherein said device comprises isolated human cells stably transfected with the (i) a recombinant expression vector comprising an isolated modified chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the modified chimeric nucleic acid sequence constitutively, wherein the modified chimeric nucleic acid sequence is shown in SEQ ID NO:8; (ii) a second expression vector comprising an isolated nucleic acid sequence encoding human furin and a glucose-regulatable TGF-alpha promoter, wherein said promoter drives expression of the nucleotide sequence encoding human furin in a glucose-regulated manner; and (iii) a third expression vector comprising an isolated nucleic acid sequence encoding proinsulin, a furin cleavable site between the human pro-insulin leader sequence and insulin sequence and a constitutive promoter which drives the expression of the nucleic acid sequence encoding proinsulin constitutively; wherein the isolated stably transfected cells express a therapeutically effective amount of GLP-1 and insulin in a glucose-dependent manner GLP-1 upon stimulation with a concentration of glucose in the blood of the subject, wherein the stimulating concentration of glucose is higher than an ambient concentration of glucose.

A further embodiment of the present invention is a method of treating a subject having Type II diabetes, said method comprising: implanting into the subject an immunoisolatory device, wherein said device comprises isolated human cells stably transfected with (i) a recombinant expression vector comprising an isolated chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the chimeric nucleic acid sequence constitutively, wherein the chimeric nucleic acid sequence is shown in SEQ ID NO:6; (ii) a second expression vector comprising an isolated nucleic acid sequence encoding human furin and a glucose-regulatable TGF-alpha promoter, wherein said promoter drives expression of the nucleotide sequence encoding human furin in a glucose-regulated manner; and (iii) a third expression vector comprising an isolated nucleic acid sequence encoding proinsulin, a furin cleavable site between the human pro-insulin leader sequence and insulin sequence and a constitutive promoter which drives the expression of the nucleic acid sequence encoding proinsulin constitutively; wherein the isolated stably transfected human cells express a therapeutically effective amount of GLP-1 and insulin in a glucose-dependent manner GLP-1 upon stimulation with a concentration of glucose in the blood of the subject, wherein the stimulating concentration of glucose is higher than an ambient concentration of glucose.

A further embodiment of the present invention is a method of treating a subject prone to hyperglycemia or suffering from hyperglycemia, said method comprising: implanting into the subject an immunoisolatory device, wherein said device comprises isolated human cells stably transfected with (i) a recombinant expression vector comprising an isolated modified chimeric nucleic acid sequence encoding a human pro-insulin leader, a glucagon-like peptide-1 (GLP-1)((7-37), a furin cleavable site between the human pro-insulin leader and the GLP-1(7-37), and a constitutive promoter which drives the expression of the nucleic acid sequence encoding GLP-1 constitutively, wherein the modified chimeric nucleic acid sequence is shown in SEQ ID NO:8, (ii) a second expression vector comprising an isolated nucleic acid sequence encoding human furin and a glucose-regulatable TGF-alpha promoter, wherein said promoter drives expression of the nucleotide sequence encoding human furin in a glucose-regulated manner, and (iii) a third expression vector comprising an isolated nucleic acid sequence encoding proinsulin, a furin cleavable site between the human pro-insulin leader sequence and insulin sequence and a constitutive promoter which drives the expression of the nucleic acid sequence encoding proinsulin constitutively; wherein the isolated stably transfected cells express a therapeutically effective amount of GLP-1 and insulin in a glucose-dependent manner upon stimulation with a concentration of glucose in the blood of the subject, wherein a stimulating concentration of glucose is higher than an ambient concentration of glucose, thereby reducing glucose blood level.

Alternatively, the present invention provides a method of treating a subject prone to hyperglycemia or suffering from hyperglycemia, said method comprising: implanting into the subject an immunoisolatory device, wherein said device comprises isolated human cells stably transfected with (i) a recombinant expression vector comprising an isolated chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the chimeric nucleic acid sequence constitutively, wherein the chimeric nucleic acid sequence is shown in SEQ ID NO:6, (ii) a second expression vector comprising an isolated nucleic acid sequence encoding human furin and a glucose-regulatable TGF-alpha promoter, wherein said promoter drives expression of the nucleotide sequence encoding human furin in a glucose-regulated manner, and (iii) a third expression vector comprising an isolated nucleic acid sequence encoding proinsulin, a furin cleavable site between the human pro-insulin leader sequence and insulin sequence and a constitutive promoter which drives the expression of the nucleic acid sequence encoding proinsulin constitutively; wherein the isolated stably transfected human cells express a therapeutically effective amount of GLP-1 and insulin in a glucose-dependent manner GLP-1 upon stimulation with a concentration of glucose in the blood of the subject, wherein the stimulating concentration of glucose is higher than an ambient concentration of glucose, thereby reducing glucose blood level.

In another embodiment, there is provided a method of reducing weight in a subject, said method comprising: implanting into the subject an immunoisolatory device, wherein said device comprises isolated human cells stably transfected with (i) a recombinant expression vector comprising an isolated modified chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the nucleic acid sequence encoding GLP-1 constitutively, wherein the modified chimeric nucleic acid sequence is shown in SEQ ID NO:8, (ii) a second expression vector comprising an isolated nucleic acid sequence encoding human furin and a glucose-regulatable TGF-alpha promoter, wherein said promoter drives expression of the nucleotide sequence encoding human furin in a glucose-regulated manner, and (iii) a third expression vector comprising an isolated nucleic acid sequence encoding proinsulin, a furin cleavable site between the human pro-insulin leader sequence and insulin sequence and a constitutive promoter which drives the expression of the nucleic acid sequence encoding proinsulin constitutively; wherein the isolated stably transfected cells express a therapeutically effective amount of GLP-1 and insulin in a glucose-dependent manner upon stimulation with a concentration of glucose in the blood of the subject, wherein the stimulating concentration of glucose is higher than an ambient concentration of glucose, wherein the GLP-1 and insulin expression reduces the weight of the subject.

There is provided herein a method of reducing weight in a subject, said method comprising: wherein said device comprises isolated human cells stably transfected (i) a recombinant expression vector comprising an isolated chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the chimeric nucleic acid sequence constitutively, wherein the chimeric nucleic acid sequence is shown in SEQ ID NO:6, (ii) a second expression vector comprising an isolated nucleic acid sequence encoding human furin and a glucose-regulatable TGF-alpha promoter, wherein said promoter drives expression of the nucleotide sequence encoding human furin in a glucose-regulated manner, and (iii) a third expression vector comprising an isolated nucleic acid sequence encoding proinsulin, a furin cleavable site between the human pro-insulin leader sequence and insulin sequence and a constitutive promoter which drives the expression of the nucleic acid sequence encoding proinsulin constitutively; wherein the isolated stably transfected cells express a therapeutically effective amount of GLP-1 and insulin in a glucose-dependent manner upon stimulation with a concentration of glucose in the blood of the subject, wherein the stimulating concentration of glucose is higher than an ambient concentration of glucose, wherein the GLP-1 and insulin expression reduces the weight of the subject.

In another embodiment of the present invention, there are provided methods of treating a subject having Type II diabetes, treating a subject prone to hyperglycemia or suffering from hyperglycemia, and reducing weight in a subject, said methods comprising implanting into the subject an immunoisolatory device containing constitutive GLP-1 producing cells, as described below. The cells produce a therapeutically effective amount of GLP-1 constitutively.

A method of treating a subject having Type II diabetes, said method comprising: implanting into the subject an immunoisolatory device, wherein said device comprises isolated human cells stably transfected with (a) a recombinant expression vector comprising an isolated modified chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the nucleic acid sequence encoding GLP-1 constitutively, wherein the modified chimeric nucleic acid sequence is shown in SEQ ID NO:8 or (b) a recombinant expression vector comprising an isolated chimeric nucleic acid sequence encoding a human pro-insulin leader, a glucagon-like peptide-1 (GLP-1)((7-37), a furin cleavable site between the human pro-insulin leader and the GLP-1(7-37), and a constitutive promoter which drives the expression of the chimeric nucleic acid sequence constitutively, wherein the chimeric nucleic acid sequence is shown in SEQ ID NO:6, wherein said cell produces endogenous furin. In another embodiment, the GLP-1 is GLP-1 (7-36) rather than GLP-1(7-37).

A method of treating a subject prone to hyperglycemia or suffering from hyperglycemia, said method comprising implanting into the subject an immunoisolatory device, wherein said device comprises isolated human cells stably transfected with (a) a recombinant expression vector comprising an isolated modified chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the nucleic acid sequence encoding GLP-1 constitutively, wherein the modified chimeric nucleic acid sequence is shown in SEQ ID NO:8 or (b) a recombinant expression vector comprising an isolated chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the chimeric nucleic acid sequence constitutively, wherein the chimeric nucleic acid sequence is shown in SEQ ID NO:6, wherein said cell produces endogenous furin. In a further embodiment, the GLP-1 is GLP-1 (7-36) rather than GLP-1(7-37).

Insulin production by pancreatic beta cells is thereby stimulated by the constitutively produced GLP-1 during an increase in glucose blood level in the patient. Advantageously, the methods of treatment may also include the implantation of engineered cells co-expressing furin and insulin, (in addition to implanted cells expressing GLP-1), which are also capable of producing insulin in glucose-regulated manner. The engineered cells insulin would provide an added therapeutic benefit for diabetic patients where endogenous insulin is not sufficient and also to cover the critical period until insulin producing pancreatic beta cells being responding to secreted GLP-1. The effect of the insulin production is reduction of the glucose blood level in the subject, thereby treating the Type II diabetes or the hyperglycemia.

In another embodiment, there is provided a method of reducing weight in a subject, said method comprising implanting into the subject an immunoisolatory device, wherein said device comprises isolated human cells stably transfected with (a) a recombinant expression vector comprising an isolated modified chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the nucleic acid sequence encoding GLP-1 constitutively, wherein the modified chimeric nucleic acid sequence is shown in SEQ ID NO:8 or (b) a recombinant expression vector comprising an isolated chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the chimeric nucleic acid sequence constitutively, wherein the chimeric nucleic acid sequence is shown in SEQ ID NO:6, wherein said cell produces endogenous furin. In a further embodiment, the GLP-1 is GLP-1 (7-36) rather than GLP-1 (7-37). The effect of the insulin production is a reduction in the weight of the subject.

Further aspects, features and advantages of the present invention will become apparent to those of ordinary skill in the art upon reading and understanding the following detailed description.

BRIEF DESCRIPTION OF THE DRAWINGS

FIG. 2 depicts the amino acid sequence of active GLP-1 peptide (SEQ ID NO: 9). The highlighted residues are necessary for the insulinotropic effect of GLP-1.

FIG. 6 provides a sequence alignment of native (GLP-1-11.11) and modified (GLP-1 BI1.2) GLP-1 constructs, which encode chimeric human proinsulin leader/furin cleavage site/GLP-1 amino acid sequences. The native (11.11) sequence are shown in SEQ ID NO: 24 (nucleic acid) and SEQ ID NO: 5 (protein), and the modified (BI1.2) sequences are shown in SEQ ID NO: 25 (nucleic acid) and SEQ ID NO: 7 (protein), respectively. The numbers above or below the amino acid residues for each sequence represent the fraction at which that particular codon is used (Reference: Codon Usage Database at www.kazusa.or.jp/codon/). The higher frequency codon usage fraction is highlighted.

FIG. 7 illustrates the active and total GLP-1 produced by transiently-transfected 293T cells. Active GLP-1 was detected by ELISA, whereas total GLP-1 was detected by radioimmunoassay (LINCO diagnostic, Inc). Cells transfected with modified GLP-1 constructs produced higher amount of GLP-1 than the cells transfected with native GLP-1 constructs.

DETAILED DESCRIPTION OF THE INVENTION

Figure 1:
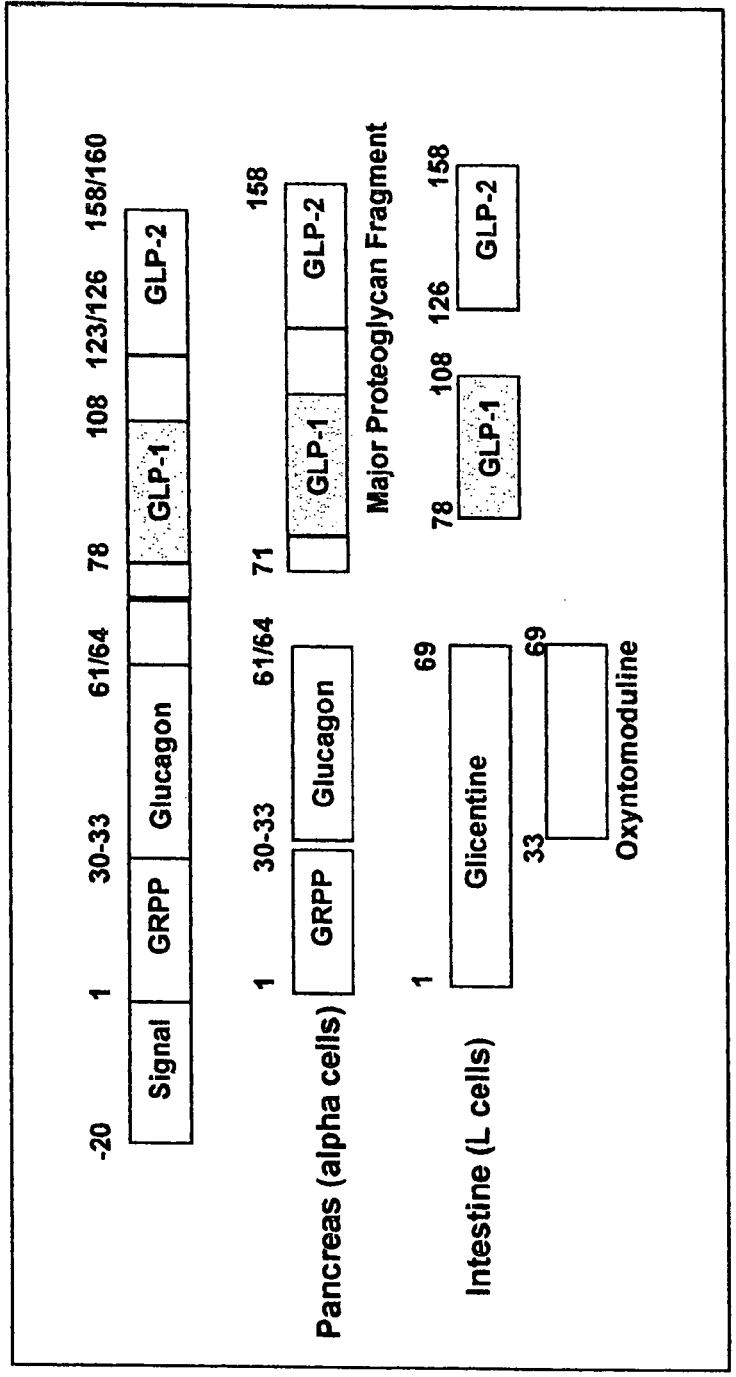
FIG. 1 illustrates pre-pro-glucagon and its major proteolysis fragments. GLP-1 is secreted as a proteolytic fragment of pre-pro-glucagon by intestinal L cells. Pre-pro-glucagon is cleaved into three two major fragments, viz., GRPP (glicentin-related polypeptide), glucagons, and MPF (major proglucagon fragment), in pancreatic alpha cells. On the other hand in intestinal L cells, the cleavage products are different and include glicentin, GLP-1, GLP-2 and oxyntomodulin. The active form of GLP-1 is generated by proteolytic cleavage at a single arginine residue at position 78.

As used herein, a "gene" is an ordered sequence of nucleotides located in a particular position on a particular chromosome (DNA) that encodes a specific functional product (i.e., a protein or RNA molecule). As used herein, a "nucleotide" is a subunit of DNA or RNA consisting of a nitrogenous base (adenine, guanine, thymidine, or cytosine in DNA; adenine, guanine, uracil, or cytosine in RNA), a phosphate molecule, and a sugar molecule. Nucleotides are linked to form a DNA or RNA molecule. Three nucleotides form a "codon" that encodes a single amino acid in a protein sequence.

As used herein, a "start codon" is usually but not exclusively ATG (AUG in the mRNA) that signals the start of a gene sequence to be translated to protein; this codon encodes the amino acid methionine (Met). A "Kozak sequence" is a DNA sequence that surrounds the ATG (AUG) start signal for the translation of an mRNA. The Kozak consensus sequence was originally defined as ACCAUGG following an analysis of the effects of single mutations surrounding the initiation codon (AUG) on translation of the preproinsulin gene by Kozak. (Kozak, M. Cell 44,283 (1986). Subsequent mutagenesis studies and a survey of 699 vertebrate mRNAs extended the consensus sequence for translation initiation to GCCGC-CACCAUGG.

As used herein, a "sense" strand is a strand of double-stranded DNA that acts as the template strand for RNA synthesis. Typically only one gene product is produced per gene, reading from the sense strand only.

As used herein, an "antisense" strand is DNA or RNA composed of the complementary sequence to a target DNA/RNA, which binds to the target DNA or RNA by base-pairing and prevents that DNA/RNA fragment from being used to synthesize new proteins, i.e., prevents expression of the target gene. As used herein, an "antisense oligonucleotide" is a short sequence of nucleotides that can bond to messenger RNA (mRNA) and block the process of gene expression. As used herein, "complementary DNA" (cDNA) is a DNA strand copied from mRNA using reverse transcriptase.

As used herein, a "gene construct" is a DNA sequence comprising a promoter, a gene of interest (nucleic acid encoding one or more native or non-native protein(s)) and regulatory elements. "Gene construct" is used interchangeably herein with "nucleic acid construct." A gene construct may contain more than one gene of interest, wherein each such gene has its own promoter and regulatory element. A "chimeric nucleic acid," as used herein, is a nucleic acid sequence comprising two or more nucleic acid sequences encoding two or more respective amino acid sequences, said nucleic acid sequences being from two or more sources, e.g., the nucleic acid sequences do not naturally exist together in the nucleic acid sequence of a gene and/or are not expressed together from one naturally occurring nucleic acid sequence. Moreover, the respective nucleic acid sequences present in chimeric nucleic acid may originate from two or more different cell type of an animal and/or from tow or more different species. Two or more nucleic acid acids in a chimeric nucleic acid may originate from the same species from two different genes or cells. Each nucleic acid sequence of which a chimeric nucleic acid is comprised has its own promoter sequence (i.e., a nucleic acid encoding said promoter) and other nucleic acid sequences required for the expression of the respective encoded amino acid sequences, i.e., peptide(s) or protein(s). For example, the isolated chimeric nucleic acid sequence may be a chimeric sequence encoding a human proinsulin leader amino acid sequence, a native GLP-1 peptide sequence and a furin cleavage site between the human proinsulin leader amino acid sequence and the native GLP-1 peptide sequence or a modified chimeric sequence encoding a human proinsulin leader amino acid sequence, an optimized GLP-1 and a furin cleavage site between the human proinsulin leader amino acid sequence and the optimized GLP-1 peptide sequence. The chimeric and modified chimeric sequences may encode GLP-1 which is GLP-1(7-37) or GLP-1(7-36).

As used herein, a "reporter gene" is a gene whose phenotypic expression is easy to monitor and is used to study gene expression, e.g., promoter activity. Recombinant DNA constructs, i.e., those made by genetic engineering, may include a reporter gene which is attached to a promoter of particular interest so that expression of the reporter gene can be used to assay promoter function once the construct is transfected into a cell. For example, a gene encoding a product which confers antibiotic resistance and renders the host cell resistant to the particular antibiotic when the cell is grown in media containing the antibiotic may serve as a "selectable marker" or reporter of promoter activity.

Zeocin™ is an antibiotic in the bleomycin family and has a broad spectrum of activity, e.g., against bacteria, eucaryotic microorganisms, plants and animal cells, making it useful as a selective marker for cells harboring vectors carrying the Zeocin™ resistance gene. (http://www.cayla.com/support/datasheets/zeotech.pdf). Expression of the Zeocin™ resistance gene ($Zeo^r$, i.e., the Sh ble gene), which encodes a protein that inactivates Zeocin™ by binding to the antibiotic, allows for the selection of drug-resistant cells after gene transfer. Zeocin™ also can be used to select cells resistant to other selective agents, i.e., G-418, Hygromycin B, Blasticidin or Puromycin, because there is no cross resistance with other currently used drug resistance markers. Other drug resistance genes may be used, including but not limited to, the ampicillin-resistance gene ($amp^r$) expresses the enzyme, β-lactamase, to inactivate the antibiotic ampicillin, and the neomycin resistance gene ($Neo^r$) which confers resistance to neomycin-kanamycin antibiotics.

As used herein, an "amino acid" is a nitrogen-containing acid, which is the basic building block of a protein. All amino acids contain an amino ($NH_2$) end, a carboxyl end (COOH) and a side group (R). In proteins, amino acids are joined together when the $NH_2$ group of one forms a bond with the COOH group of the adjacent amino acid. There are 20 common amino acids in animals and humans: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

As used herein, a "peptide" or a "polypeptide" is a linkage of up to about 50 amino acids to form a chain. "Proteins" are chains of amino acids that are longer than 50 amino acids. Amino acids are coupled by a peptide bond, a linkage in which the nitrogen atom of one amino acid binds to the carboxyl carbon atom of another.

As used herein, GLP-1 means an active human glucagon-like peptide-1 GLP-1(7-37) whose amino acid sequence is HAEGTFTSDVSSYLEGQAAKEFIAWLVKGRG [SEQ ID NO: 9] or GLP-1(7-36) whose amino acid sequence is HAEGTFTSDVSSYLEGQAAKEFIAWLVKGR [SEQ ID NO: 10] or variants thereof. Preferably the GLP-1 is GLP-1(7-37) or a variant thereof. In another embodiment, the GLP-1 is GLP-1 (7-36) amide or variant thereof. A "variant" of GLP-1 as used herein means an amino acid sequence in which one or more amino acids have been altered from the native sequence by one or more substitution, deletion or insertion of an amino acid residue without changing the activity of the GLP-1, i.e., a "GLP-1 variant" may have one or more amino acid residue deletions and thus will be shorter than GLP-1 (7-36), i.e., a fragment of GLP-1, but will the same activity as the native GLP-1 sequence, e.g., in stimulating insulin secretion by pancreatic beta cells, by virtue of having the amino acid residues which are critical for GLP-1 activity or residues which may be substituted for one or more of these critical residues. See FIG. 2, underlined residues H, G, F, T, D, F and I. For example, in a GLP-1 variant, isoleucine, i.e., a neutral non-polar amino acid residue may be substituted with another non-polar amino acid having branched hydrocarbon side chains such as leucine or valine. One of skill will readily determine whether an amino acid residue may be substituted by another amino acid residue based on its classification in one of the four different classes of amino acids, which are determined by different side chains: (1) non-polar and neutral, (2) polar and neutral, (3) acidic and polar, (4) basic and polar.

As used herein, "insulin" means the biologically active peptide hormone produced by the beta cells of the islets on Langerhans in the pancreas. In its active form, insulin is comprised of two separate chains, the A and B chains, which consist of 21 and 30 amino acids respectively and three disulfide bridges, two between the A and B chains and one. Insulin is synthesized as a single inactive peptide known as "preproinsulin", which has a leader (or signal) sequence, the B chain, a connecting "C" peptide and the A chain. The leader sequence provides a signal to the cell to deposit the proinsulin outside the cell. The leader sequence of preproinsulin is cleaved by a peptidase as it is transported into the rough endoplasmic reticulum, then two of the three disulfide bridges are formed resulting in proinsulin. The C-peptide is cleaved by a second peptidase and an internal disulfide bridge is formed to produce insulin. Endogenous insulin has a half-life of about four minutes and the half-life C-peptide is about 30 minutes.

As used herein, a human "proinsulin leader" means the preproinsulin signal sequence whose amino acid sequence is MALWMRLLPLLALLALWGPDPAAA.

As used herein, an "expression vector" is a cloning vector that is engineered to allow the expression of protein from a cDNA, i.e., its coding sequence is properly transcribed and the RNA is translated. The expression vector provides an appropriate promoter sequence for the initiation of transcription and restriction sites that allow insertion of cDNA. A "plasmid," which is a small, circular DNA molecule capable of autonomous replication in a cell, is commonly used as a cloning vector. Various plasmids are available commercially, including plasmids containing a promoter, cloning sites and an antibiotic resistance gene. For example, plasmid vectors pcDNA3.1(+) and pcDNA3.1(-) are designed for high-level stable and transient expression in mammalian hosts; the vectors contain a human cytomegalovirus immediate-early (CMV) promoter for high-level expression in a wide range of mammalian cells, multiple cloning sites in the forward (+) and reverse (-) orientations to facilitate cloning, a neomycin resistance gene for selection of stable cell lines and episomal replication in cell clones that are latently infected with SV40 or that express the SV40 large T antigen, e.g., COS-1 and COS-7. (www.invitrogen.com). Plasmid pcDNA3.1/Zeo, also available from Invitrogen™, contains among other features a CMV promoter, SV40 promoter and origin, Zeocin™ resistance gene, bla promoter, and an ampicillin (bla) resistance gene. (http://www.invitrogen.com/content/sfs/vectors/pcdna3.1zeo_map.pdf).

As used herein, the terms "modified nucleic acid sequence" and "optimized nucleic acid sequence" are used interchangeably and are intended to mean a nucleic acid sequence whose codons have been synthesized using an algorithm to select the preferred codon used in a genome of a particular species, e.g., from the human genome, to encode a specific amino acid. Due to the degeneracy of the genetic code, an amino acid may have more than one codon encoding it at the nucleic acid level. A nucleic acid encoding a protein, e.g., a non-naturally occurring protein whose amino acid sequence is based on a protein human sequence, may be difficult to express; an optimized non-natural nucleic acid sequence for the naturally occurring protein is advantageous because it may enable over-expression of the naturally occurring protein.

As used herein "constitutive" means a gene is expressed in an unregulated fashion, i. e., constitutive for the production of an enzyme or other protein if that protein is always produced by the cells under all physiological conditions, e.g., GLP-1 that is produced continuously regardless of glucose concentration. The CMV promoter is a "constitutive promoter", i.e., under whose control the expression of a nucleic acid sequence does not depend upon a triggering agent, i.e., an inducer. In contrast, "inducible" or "regulated" or "inducer agent-dependent" transcription is triggered by inducers, small molecules able to act on regulating sequences of these genes, e.g., GLP-1 that is produced in a "glucose-dependent," i.e., regulated/inducible manner, for example after ingestion of nutrients when blood sugar increases.

As used herein, "transforming growth factor alpha" (TGF-alpha) is a 50 amino acid secreted polypeptide sharing 35% sequence homology with EGF. TGF-alpha binds to the EGF receptor and like EGF, is a potent mitogen for several cell types. The 5' end of the TGF-α transcript (i.e., messenger RNA synthesized from DNA) has been localized to a single site of transcription initiation; no CCAAT or TATA sequences are present in the TGF-α promoter sequence, suggesting that transcription can initiate at unique and specific positions from promoters lacking this sequence motif. (Jakobovits, et al. Mol. Cell. Biol. December 1988, Vol. 8, No. 2, 5549-5554) TGF-α promoter is a preferred glucose-regulatable promoter and has been found to useful in the glucose regulated expression of human subtilisin-like proteases, e.g., furin. (Tatake et al., U.S. Patent Application Publication US 2003/0032144, Feb. 13, 2003, now U.S. Pat. No. 7,045,346)

As used herein, a "transformed" cell is a cell that has been genetically altered by the introduction, uptake and expression of exogenous, i.e., "foreign" or originating outside the organism or cell genetic material (DNA or RNA).

As use herein, "furin" means a ubiquitous subtilisin-like proprotein convertase, which is a mammalian enzyme involved in the cleavage of many constitutively expressed protein precursors. The minimal "furin cleavage site" is Arg-X-X-Arg', however, the enzyme prefers the site Arg-X-(Lys/Arg)-Arg'.

The term "implanting" as used herein means transplanting or introducing cells into a subject, wherein the cells remain "functional" after implantation for a period of time, e.g., ≧14 days. Cells implanted in an immunoisolatory devices may be functional up a year. See Long-term erythropoietin gene expression from transduced cells in bioisolator devices. Hum. Gene Ther. 2003 Nov. 20;14(17);1587-93, which is hereby incorporated by reference in its entirety. The term "functional" as used herein means performing a desired function, e.g., the cell expresses a protein from an expression vector transformed into the cell, such as GLP-1, insulin, and/or furin, whose expression is driven by a constitutive promoter or a substrate-dependent promoter, e.g., a glucose-dependent promoter. The introduced cells preferably are cells transformed with a nucleic acid construct. Preferably, the construct comprises a recombinant nucleic acid encoding proinsulin leader/furin cleavage site/GLP-1 in a tandem sequence. More preferably, the nucleic acid sequence is an optimized nucleic acid sequence encoding proinsulin leader/furin cleavage site/GLP-1 in a tandem sequence.

As used herein, an "immunoisolatory device" is a vehicle in which functional cells secreting a therapeutic peptide, polypeptide or protein are encapsulated in synthetic membranes which protect the cells from immune system rejection without any immunosuppression, but allow nutrients to diffuse into and therapeutic agents, e.g., proteins, secreted by the cells to diffuse out of the device. Preferably, the device is adapted for removal of cells and replacement thereof with fresh cells producing the same or different therapeutic agents. The device is biocompatible, i.e., does not cause injury, is not toxic and produces no immunologic reaction to living tissue, e.g., the human body, into which it is implanted. Preferably, the cells are allogeneic and have been genetically engineered to secrete recombinant therapeutic protein(s). The cells may be dispersed or immobilized in a matrix or suspended in a liquid medium, e.g., as described in U.S. Pat. No. 5,869,077 to Dionne or PCT/US99/08628 to Powers et al. TheraCyte® is a commercial immunoisolatory device which has a retrievable chamber designed to function subcutaneously and enable long term allogeneic cell transplantation. (www.theracyte.com). Such devices have protected allogeneic tissues in non-immunosuppressed humans for more than one year, as well as insulin secreting cells in diabetic (NOD) mice and Factor IX secreting human cells in athymic mice and rats for up to a year. (http://www.gtmb.org/gene-therapy-conferences/abstracts_2001/Abstract_Loudovaris.htm).

As used herein "treating" means to improve or provide a remedy for a disease or disorder, e.g., by lessening the symptoms thereof. "Diabetes," as used herein means Type II diabetes, non-insulin dependent mellitus and a diabetic subject is one who suffers from diabetes by exhibiting some or all of the symptoms of diabetes. A symptom of diabetes includes a high blood glucose level. A fasting blood glucose (after an 8 hour fast) of 126 mg/dL (7.00 mmol/L) or higher is consistent with either Type I or Type II diabetes when accompanied by classic symptoms of diabetes, e.g., increased thirst or hunger, frequent urination, weight loss or blurred vision. A fasting blood sugar of 100 mg/dL (5.55 mmol/L) to 125 mg/dL (6.94 mmol/L), may indicate a state of pre-diabetes, which affects about 16 million American adults. "Pre-diabetes" as used herein is an impaired glucose tolerance, which occurs when blood glucose levels are higher than normal, but still not at the 126 mg/dL or higher level that qualifies for a bona fide diabetes diagnosis. A "pre-diabetic" subject is one who exhibits such an impaired glucose tolerance but not reaching the fasting glucose levels of a diabetic. A normal fasting blood sugar level is now 99 mg/dL or lower, i.e., 70 milligrams per deciliter (mg/dL), or 3.88 millimoles per liter (mmol/L), to 99 mg/dL. Normal blood glucose levels will vary from individual to individual depending upon the person's sex, age, weight, diet and health.

Untreated high blood sugar from Type II diabetes significantly increases the risk of having a heart attack or stroke, as well as developing kidney failure, blindness, or blocked blood vessels in the legs that can lead to amputations. Accordingly, as used herein, treating or treatment of diabetes includes a decrease in blood glucose levels compared to pretreatment levels or to a diabetic patient. Treatment of diabetes includes the treatment of conditions or complications associated with diabetes, including but not limited to, heart disease (cardiovascular disease), high blood pressure, peripheral vascular disease, coronary artery disease, cerebral vascular disease, blindness (retinopathy), glaucoma, nerve damage (neuropathy), kidney damage (nephropathy), and periodontal (gum) disease.

Treatment of high glucose levels in a non-diabetic patient, i.e., in a hyperglycemic state, means a lowering of a high blood glucose level to a normal blood glucose level, i.e., between 70 and 99 mg/dL, or reduced from the high level to a level above hypoglycemia.

As used herein, a "therapeutically effective amount" means an amount sufficient to render a disease condition better or to improve one or more symptoms associated with the disease.

"Overweight" as used herein means having a ratio of body weight to height, i.e., body mass index (BMI) of 25 up to 29.9 kg/m2. "Obese" as used herein means having a high amount of body fat and having a body mass index (BMI) of 30 kg/m2 or greater. Treatment of obese and overweight patients means decreasing the respective BMIs to below the above-defined ranges, i.e., from an obese BMI to an overweight or normal BMI or and from an overweight BMI to a normal BMI.

The present invention is directed to genetically engineered cells and uses of such cells for the treatment of diabetes, hyperglycemia in non-diabetic or pre-diabetic patients, as well as for reduction of weight in the diabetic, pre-diabetic and non-diabetic patients. The therapeutic methods provided herein involve the implantation of genetically engineered cells into the aforementioned subjects for the production of active human GLP-1.

The genetically engineered cells comprise an isolated chimeric GLP-1 optimized (modified) nucleic acid sequence encoding a human pro-insulin leader/furin cleavable site/a glucagon-like peptide-1 (GLP-1) in a tandem sequence, i.e., the furin cleavable site is between the human pro-insulin leader sequence and the GLP-1. Preferably, the isolated modified chimeric nucleic acid sequence used to engineer the cells encodes GLP-1 peptide, GLP-1(7-37) [SEQ ID NO:9], which is shown in FIG. 2, or GLP-1(7-36) [SEQ ID NO:10], which has a sequence similar to the sequence shown in FIG. 2 but includes residues 7-36 and lacks the final glycine residue (i.e., lacks amino acid residue 37 found in GLP-1(7-37)). In an embodiment, the isolated modified chimeric protein sequence is SEQ ID NO:7. In an embodiment, the isolated modified chimeric nucleic acid sequence is SEQ ID NO: 8. In an alternate embodiment, the isolated modified chimeric modified protein sequence has a sequence similar to SEQ ID NO:7, but in which the encoded GLP-1 is GLP-1(7-36) [SEQ ID NO:10], which lacks the final glycine residue of GLP-1 (7-37). Also provided is a modified chimeric nucleic acid sequence, which includes the nucleic acid sequence encoding GLP-1(7-36), which lacks the codon GGA encoding glycine.

In another embodiment, the genetically engineered cells comprise an isolated chimeric (native) GLP-1 nucleic acid sequence encoding a human pro-insulin leader/furin cleavable site/a native glucagon-like peptide-1 (GLP-1) in a tandem sequence, i.e., the furin cleavable site is between the human pro-insulin leader sequence and the native GLP-1. Preferably, the isolated chimeric nucleic acid sequence used to engineer the cells encodes native GLP-1 peptide, i.e., GLP-1(7-37) or GLP-1(7-36). In an embodiment, the isolated chimeric native GLP-1 protein sequence is SEQ ID NO:5. In another embodiment, the isolated chimeric (native) GLP-1 nucleic acid sequence is SEQ ID NO:6. In an alternate embodiment, the isolated chimeric (native) protein sequence has a sequence similar to SEQ ID NO:5, but in which the encoded GLP-1 is GLP-1(7-36) [SEQ ID NO:10], which lacks the final glycine residue of GLP-1(7-37). Also provided is a chimeric nucleic acid sequence, which includes the nucleic acid sequence encoding GLP-1(7-36), which lacks the codon GGA encoding glycine.

Figure 3:
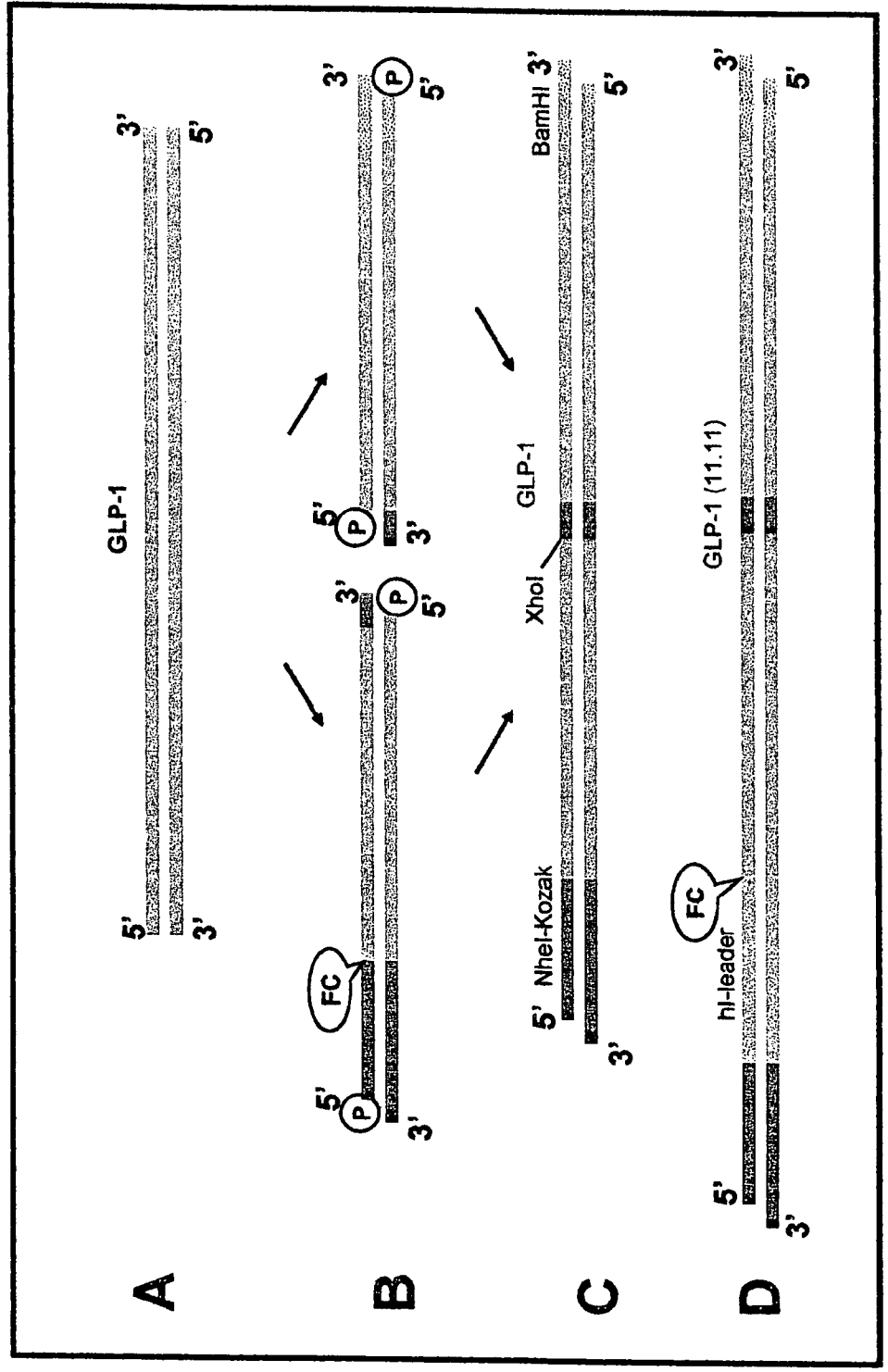
FIG. 3 is a diagrammatic representation of cloning strategy for GLP-1

The preparation of a native GLP-1 construct is illustrated in FIG. 3. A XhoI restriction site was added at the midpoint of the GLP-1 encoding nucleic acid sequence, creating an N-terminal and a C-terminal fragment. A furin cleavage site, the Kozak sequence and NheI restriction site were inserted at the 5' end of the N-terminal fragment of GLP-1. A BamHI restriction site was added to the 3' end of the C-terminal fragment. All oligonucleotides were phosphorylated.

A pCDNA3.1 expression vector was used to subclone the N-terminal and C-terminal fragments, as described in Example 1. A nucleic acid encoding the human proinsulin leader was PCR amplified and subcloned upstream of the furin cleavage site, as shown in FIG. 3D.

Figure 4:
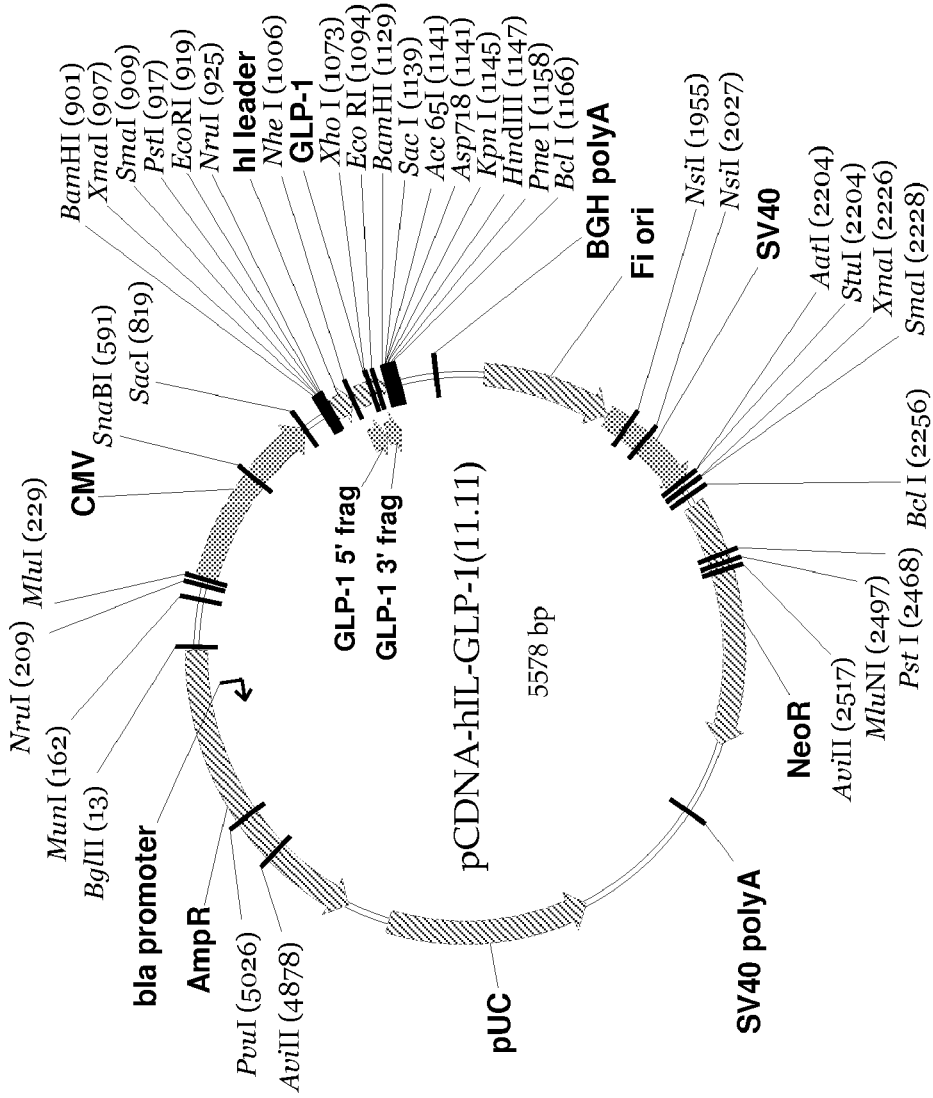
FIG. 4 illustrates a vector map of a native GLP-1 construct.

FIG. 4 illustrates a vector map of the resulting native GLP-1 construct, which encodes a chimeric protein comprising the human proinsulin leader, the furin cleavage site and native GLP-1. The plasmid, designated pCDNA-hIL-GLP-1 (11.11) includes nucleic acids encoding a constitutive CMV promoter, a human proinsulin leader and GLP-1, i.e., the cDNA encoding human proinsulin leader sequence and GLP-1(7-37), respectively, which has a furin cleavage site therebetween, a bla promoter and the ampicillin (bla) resistance gene driven by this promoter, NeoR, the sequence encoding neomycin phosphotransferase, a selectable marker gene, and its promoter SV40. A constitutive promoter other than CMV may be used.

In order to engineer human cells to produce GLP-1(7-37) constitutively, the present invention provides a recombinant expression vector comprising an isolated chimeric GLP-1 optimized nucleic acid sequence encoding a human pro-insulin leader, a glucagon-like peptide-1 (GLP-1) (7-37), a furin cleavable site between the human pro-insulin leader and the GLP-1 (7-37), and a CMV promoter. Human cells produce furin endogenously and will cleave the furin cleavable site to produce GLP-1. Preferably, the expression vector is a plasmid. Advantageously, the expression vector produces GLP-1 in a constitutive manner, i.e., always expresses the GLP-1 in an unregulated fashion (not under the control of a substrate-regulated promoter, e.g., not controlled by a substrate such as glucose). A stably transfected cell comprising such a GLP-1 producing expression vector may be implanted into a patient to produce GLP-1; any GLP-1 produced by the engineered cells which is not used, i.e., when the body does not need to stimulate insulin production in normoglycemia, i.e., during normal blood glucose levels, is degraded by the body's native DPPIV. A human cell may be stably transfected with the above-described recombinant expression vector. In alternate embodiments, the encoded GLP-1 may be GLP-1 (7-37) or GLP-1(7-36). Preferably, the expression vector is a plasmid. If the transfected cell does not produce any furin or an insufficient endogenous amount of furin, the cell may be co-transfected with a second vector that expresses furin either in a constitutive or in a regulated manner, i.e., in the case of glucose-regulated manner, upon an increase in the concentration of glucose, i.e., furin is expressed to a level higher than an ambient concentration of glucose in the cell.

The engineered human cells which may be transfected with the GLP-1-expressing vector may be cells that have been previously stably transfected with an expression vector expressing furin-cleavable pro-insulin to produce insulin, wherein furin in expressed in a glucose-dependent manner. (See Tatake et al., U.S. Patent Application Publication US 2003/0032144; U.S. Pat. No. 7,045,346, which are hereby incorporated in their entirety into the present application.) Thus, these engineered cells have a capacity to produce both insulin and GLP-1 in a glucose-regulated manner. Both of these transfected cells, i.e., cells transfected with a GLP-1 expressing vector or transfected with GLP-1-expressing and insulin co-expressing vectors may be used in combination for treating diabetes, hyperglycemia and overweight conditions.

Figure 5:
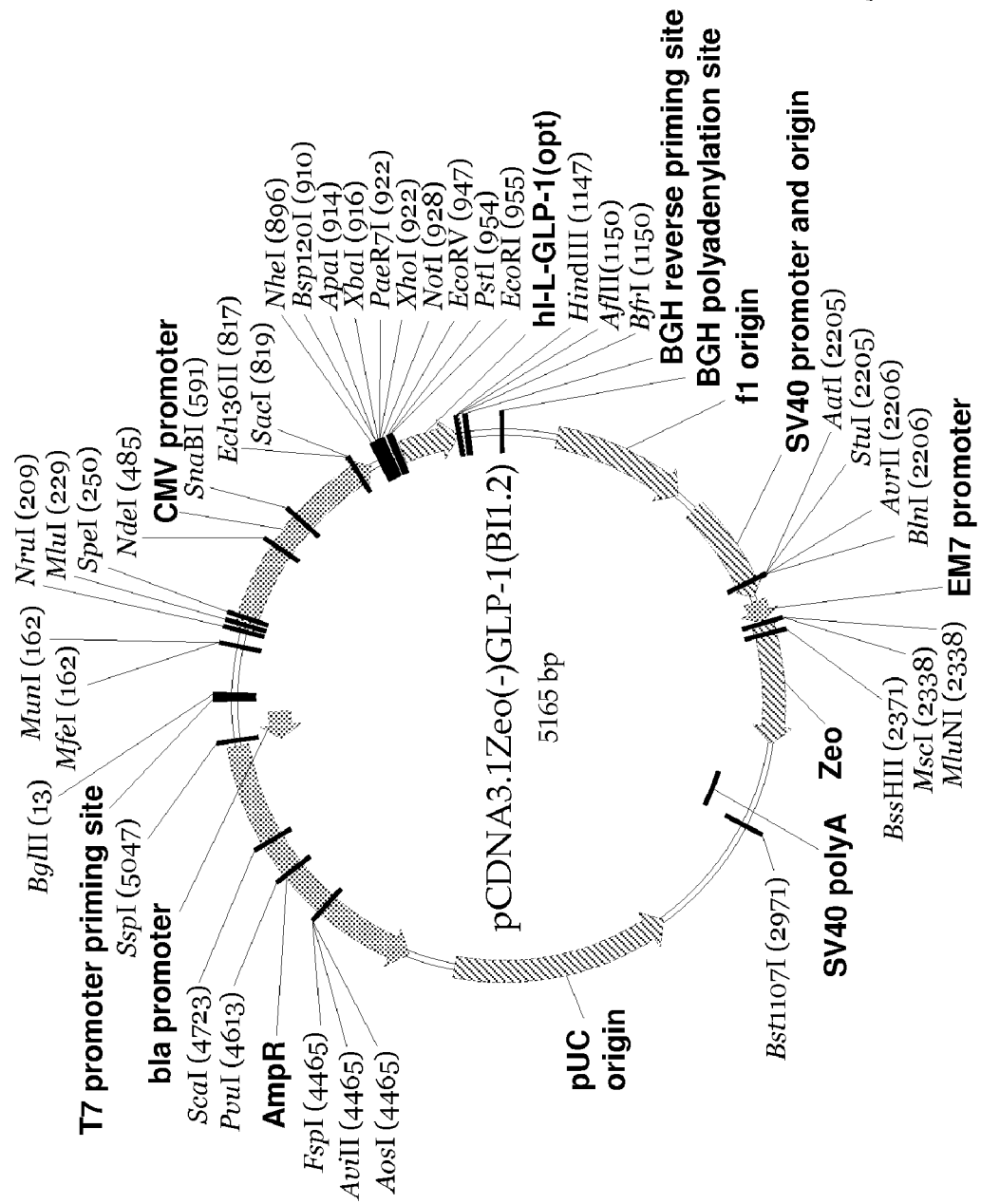
FIG. 5 shows a vector map of an GLP-1 construct comprising a modified nucleotide sequence which encodes human glucagon-like peptide-1 (GLP-1).

FIG. 5 illustrates a vector map of the optimized GLP-1 construct, which was subcloned into a pCIneo eukaryotic expression vector. The vector contains the modified chimeric nucleic acid sequence hI-GLP-1(opt) [SEQ ID NO:8] encoding a chimeric protein [SEQ ID NO: 7] comprising a human proinsulin leader, a furin cleavage site and GLP-1, wherein the GLP-1 is optimized and does not contain the amino acid sequence LLATMG before the furin cleavage site. The plasmid, designated pCDNA3.1Zeo(–)GLP-1(BI1.2) includes a CMV promoter for expression of the modified chimeric nucleic acid sequence, a Zeo resistance gene and its EM7 promoter, a bla promoter for the ampicillin (bla) resistance gene and T7 promoter priming site.

The present invention provides a recombinant expression vector comprising an isolated chimeric GLP-1 nucleic acid sequence encoding a human pro-insulin leader, a glucagon-like peptide-1 (GLP-1)(7-37), a furin cleavable site between the human pro-insulin leader and the GLP-1 (7-37), and a constitutive promoter, e.g., a CMV promoter, which drives the expression of the chimeric GLP-1 nucleic acid sequence constitutively.

The present invention also provides a recombinant expression vector comprising an isolated chimeric GLP-1 nucleic acid sequence encoding a human pro-insulin leader, a glucagon-like peptide-1 (GLP-1)(7-37), a furin cleavable site between the human pro-insulin leader and the GLP-1 (7-37), and a constitutive promoter, e.g., a CMV promoter, which drives the expression of the chimeric GLP-1 nucleic acid sequence constitutively. The expression vector may further comprising a nucleotide sequence encoding human furin and a glucose-regulatable promoter, e.g., TGF-alpha promoter, which drives the expression of the nucleotide sequence encoding human furin in a glucose-dependent manner. In this embodiment, GLP-1(7-37) is produced in a glucose-regulated manner when the glucose-regulated furin, expressed in the presence of glucose, said glucose being present in a concentration higher than an ambient glucose concentration in the cell, cleaves the furin cleavable site between the human pro-insulin leader and the GLP-1 (7-37). Alternatively, the recombinant expression vector comprises an isolated chimeric GLP-1 nucleic acid sequence encoding a human pro-insulin leader, a glucagon-like peptide-1 (GLP-1)(7-36), a furin cleavable site between the human pro-insulin leader and the GLP-1 (7-36), and a constitutive promoter, e.g., a CMV promoter, which drives the expression of the chimeric GLP-1 nucleic acid sequence constitutively.

Preferably, a human cell is stably transfected with the above-described expression vectors. Further, the human cell stably transfected with the recombinant expression vectors constitutively expressing GLP-1 produces furin endogenously. If the transfected cell does not naturally produce furin or does not produce an endogenous amount of furin sufficient for constitutive production of GLP-1 by the cell, the cell may be co-transfected with a second recombinant expression vector expressing human furin and a glucose-regulatable promoter, i.e., TGF-alpha promoter, which controls the expression of furin in a glucose dependent manner. In a co-transfected cell expressing furin in glucose-regulated manner, upon an increase in glucose concentration compared to the ambient glucose concentration, i.e., glucose present in the media or environment surrounding the cells signals, signals the TGF-alpha promoter to drive augmented expression of human furin, which then cleaves the constitutively expressed proinsulin/furin cleavage site/GLP-1 recombinant protein at the furin cleavable site to produce GLP-1. Preferably, both expression vectors are plasmids. As described below, the human cells may also be transfected with an expression vector comprising a nucleotide sequence encoding human furin and a glucose-regulatable promoter, e.g., TGF-alpha promoter, which drives the expression of the human furin in a glucose-dependent manner.

In addition, the present invention provides human cells stably transfected with a recombinant expression vector comprising an isolated chimeric GLP-1 nucleic acid sequence encoding a human pro-insulin leader, a glucagon-like peptide-1 (GLP-1)(7-37), a furin cleavable site between the human pro-insulin leader and the GLP-1(7-37), and constitutive promoter, e.g., a CMV promoter. Such cells produce GLP-1(7-37) constitutively when endogenously produced furin in the cells cleaves the a furin cleavable site and also are referred to herein as constitutive GLP-1 producing cells. In an embodiment, the isolated chimeric nucleic acid sequence is shown in SEQ ID NO:6. In a further embodiment, human cells are stably transfected with the recombinant expression vector comprising an isolated chimeric GLP-1 nucleic acid sequence encoding a human pro-insulin leader, a glucagon-like peptide-1 (GLP-1)(7-36), a furin cleavable site between the human pro-insulin leader and the GLP-1 (7-36), and a constitutive promoter, e.g., a CMV promoter, driving the expression of the chimeric GLP-1 nucleic acid sequence constitutively. In an embodiment, the isolated chimeric nucleic acid sequence has a sequence that is shorter than SEQ ID NO:6, i.e., the GLP-1 encoding nucleic acid sequence within the chimeric nucleic acid sequence lacks the codon GGA, which encodes glycine (residue 37) of GLP-1(7-37), thus, the isolated chimeric nucleic acid sequence encodes GLP-1 (7-36) peptide shown in SEQ ID NO: 10.

Further provided by the present invention are human cells stably transfected with (a) a recombinant expression vector comprising an isolated chimeric GLP-1 nucleic acid sequence encoding a human pro-insulin leader, a glucagon-like peptide-1 (GLP-1)(7-37), a furin cleavable site between the human pro-insulin leader and the GLP-1(7-37), and a constitutive promoter, e.g., a CMV promoter, which drives the expression of the isolated chimeric GLP-1 nucleic acid sequence constitutively; (b) a second expression vector comprising an isolated nucleic acid sequence encoding human furin and a glucose-regulatable TGF-alpha promoter, wherein said promoter drives expression of the nucleotide sequence encoding human furin in a glucose-regulated manner, and (c) a third expression vector comprising an isolated nucleic acid sequence encoding proinsulin, a furin cleavable site between the human pro-insulin leader sequence and insulin sequence and a constitutive promoter which drives the expression of the nucleic acid sequence encoding proinsulin constitutively. Such a human cell is engineered to express furin in glucose-regulated manner, thereby enabling (a) glucose-responsive cleavage of the co-expressed isolated chimeric GLP-1 nucleic acid sequence encoding the human pro-insulin leader, the glucagon-like peptide-1 (GLP-1)(7-37), the furin cleavable site between the human pro-insulin leader and the GLP-1(7-37) at the furin cleavable site to produce active GLP-1(7-37) as well as (b) co-expression of insulin by the furin cleavage of the proinsulin at the furin cleavable site between the human pro-insulin leader sequence and the insulin sequence. Such cells produce GLP-1 in a glucose-dependent manner and also are referred to herein as the "glucose-regulated" or "glucose-dependent" GLP-1 producing cells. An increase in glucose concentration compared to the ambient glucose concentration prompts augmented human furin expression followed by cleavage of the expressed proinsulin/furin cleavage site/GLP-1 recombinant protein at the furin cleavable site to produce GLP-1. A human cell stably transfected with the described recombinant expression vector expresses human furin, and thus GLP-1 in a glucose-dependent manner. The cells are also referred to herein as "glucose-regulated GLP-1 and insulin co-producing cells" or "glucose-dependent GLP-1 and insulin co-producing cells." In an embodiment, the isolated chimeric nucleic acid sequence is shown in SEQ ID NO:6, which encodes GLP-1(3-37). In an alternate embodiment, isolated chimeric nucleic acid sequence is shorter than the sequence shown in SEQ ID NO:6, i.e., it lacks the codon GGA, which encodes amino acid residue 37, glycine of GLP-1(7-37). In an embodiment, the isolated chimeric protein sequence is SEQ ID NO:5 in which the encoded GLP-1 is GLP-1(7-37). In an alternate embodiment, isolated chimeric protein sequence is shorter than SEQ IDNO:5 by the lack of amino acid residue 37, glycine and the encoded GLP-1 is GLP-1(7-36).

The present invention also provides a recombinant expression vector comprising an isolated modified chimeric GLP-1 nucleic acid sequence encoding a human pro-insulin leader, a glucagon-like peptide-1 (GLP-1)(7-37), a furin cleavable site between the human pro-insulin leader and the GLP-1(7-37), and a constitutive promoter, e.g., a CMV promoter, which drives the expression of the modified chimeric GLP-1 nucleic acid sequence constitutively. In an embodiment, the modified chimeric nucleic acid sequence is shown in SEQ ID NO:8. In a further embodiment, the recombinant expression vector may further comprise a nucleotide sequence encoding human furin and a glucose-regulatable promoter, e.g., TGF-alpha promoter, which drives the expression of the nucleotide sequence encoding human furin in a glucose-dependent manner. In an alternate embodiment, the recombinant expression vector comprises an isolated modified chimeric GLP-1 nucleic acid sequence encoding a human pro-insulin leader, a glucagon-like peptide-1 (GLP-1)(7-36), a furin cleavable site between the human pro-insulin leader and the GLP-1 (7-36), and a constitutive promoter, e.g., a CMV promoter, which drives the expression of the chimeric GLP-1 nucleic acid sequence constitutively.

In addition, the present invention provides human cells stably transfected with a recombinant expression vector comprising an isolated modified chimeric GLP-1 nucleic acid sequence encoding a human pro-insulin leader, a glucagon-like peptide-1 (GLP-1)(7-37), a furin cleavable site between the human pro-insulin leader and the GLP-1(7-37), and constitutive promoter, e.g., a CMV promoter. Such cells produce GLP-1 constitutively when endogenously produced furin in the cells cleaves the a furin cleavable site and are referred to herein as the constitutive GLP-1 producing cells. In an embodiment, the modified chimeric nucleic acid sequence is shown in SEQ ID NO:8. In another embodiment, the encoded GLP-1 may be GLP-1(7-36), i.e., the nucleic acid sequence is shorter than the sequence shown in SEQ ID NO:8 by the lack of the codon GGA, which codon encodes the amino acid glycine in GLP-1(7-37).

Also provided by the present invention are human cells stably transfected with (a) a recombinant expression vector comprising an isolated modified chimeric GLP-1 nucleic acid sequence encoding a human pro-insulin leader, a glucagon-like peptide-1 (GLP-1)(7-37), a furin cleavable site between the human pro-insulin leader and the GLP-1(7-37), and a constitutive promoter, e.g., a CMV promoter, which drives the expression of the modified chimeric GLP-1 nucleic acid sequence constitutively; (b) a second expression vector comprising an isolated nucleic acid sequence encoding human furin and a glucose-regulatable TGF-alpha promoter, wherein said promoter drives expression of the nucleotide sequence encoding human furin in a glucose-regulated manner, and (c) a third expression vector comprising an isolated nucleic acid sequence encoding proinsulin, a furin cleavable site between the human pro-insulin leader sequence and insulin sequence and a constitutive promoter which drives the expression of the nucleic acid sequence encoding proinsulin constitutively. Such a human cell is engineered to express furin in glucose-regulated manner, thereby enabling (a) glucose-responsive cleavage of the co-expressed isolated modified chimeric GLP-1 nucleic acid sequence encoding a human pro-insulin leader, a glucagon-like peptide-1 (GLP-1) (7-37), a furin cleavable site between the human pro-insulin leader and the GLP-1 (7-37) at the furin cleavable site to produce active GLP-1((7-37), as well as (b) co-expression of insulin by the furin cleavage of a proinsulin at the furin cleavable site between the human pro-insulin leader sequence and insulin sequence. Such cells produce GLP-1(7-37) and insulin in a glucose-dependent manner and are referred to herein as the "glucose-regulated" or "glucose-dependent" GLP-1 producing cells. The cells are also referred to herein as glucose-regulated GLP-1 and insulin co-producing cells or glucose-dependent GLP-1 and insulin co-producing cells. In an embodiment, the modified chimeric nucleic acid sequence is shown in SEQ ID NO:8. In an alternate embodiment, the encoded GLP-1 may be GLP-1(7-36) shown in SEQ ID NO:10, wherein the modified chimeric nucleic acid sequence is shorter than SEQ ID NO:8 by one codon, GGA, i.e., it does not encode amino acid residue 37, glycine, found in GLP-1 (7-37).

Human cells were engineered to produce GLP-1 in a glucose-regulated manner, as described in Example 4. Glucose-responsive insulin secreting cells (GRIS), i.e., GRIS clones, are derived from U2OS cells that were stably transfected with vectors described in patent application US 2003/003214, published Feb. 13, 2003, now U.S. Pat. No. 7,045,346, which are incorporated herein by reference in their entirety. The stably transfected parent U2OS cells contain vectors with nucleic acid sequences encoding furin cleavable proinsulin and human furin under the control of glucose-regulatable TGF-alpha promoter and produce furin, which cleaves the proinsulin to produce insulin in a glucose-dependent manner.

Figure 13:
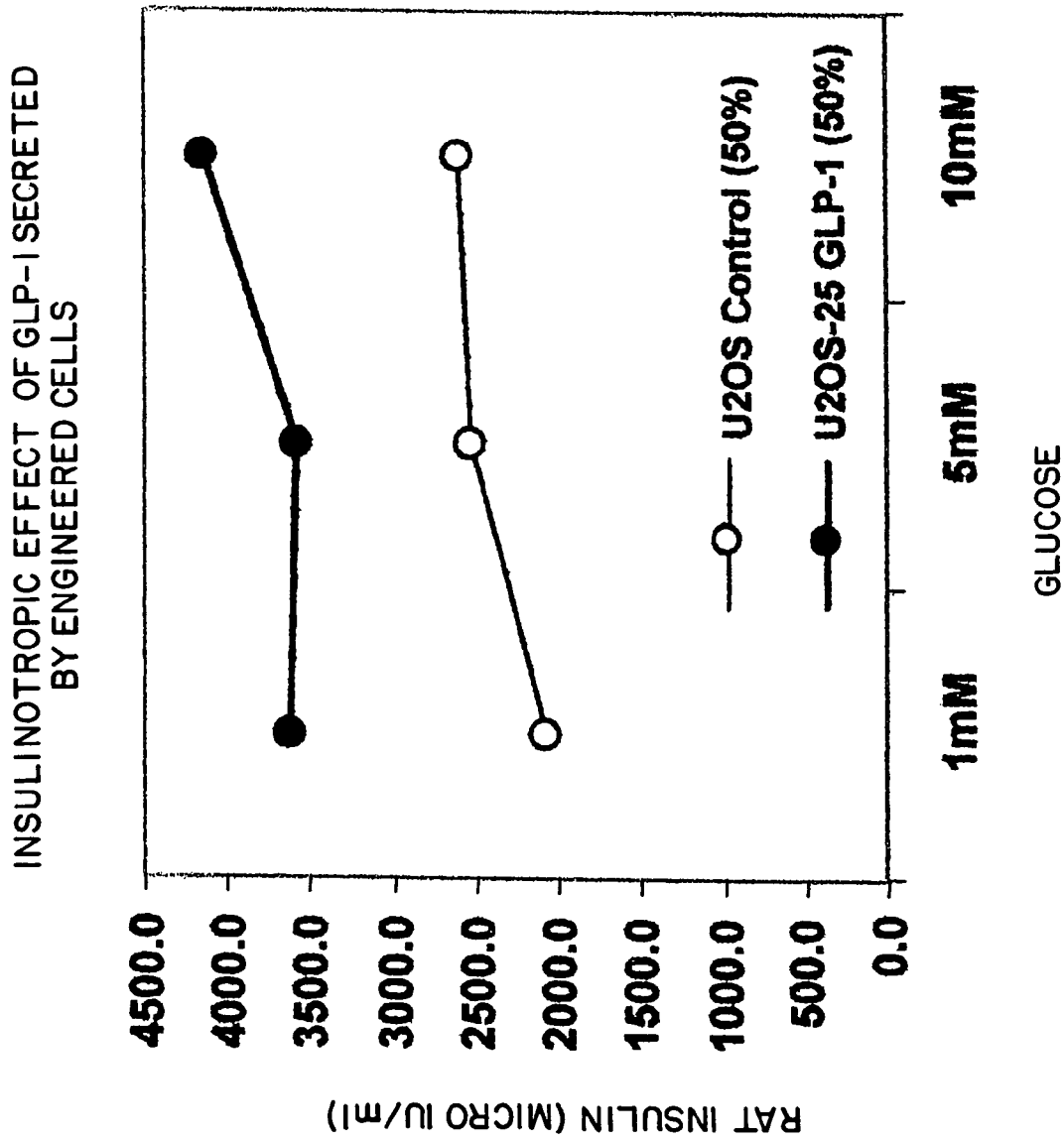
FIG. 13 shows the insulinotropic effect of GLP-1 secreted by engineered cells. Supernatants from GLP-1 producing U2OS-25 clone (which is an arbitrary designation), derived from U2OS cells stably co-transfected with native GLP-1 construct and human furin, augmented insulin production by RIN5F cells.

The GRIS cells were stably transfected with GLP cDNA. The clones were tested for their production of GLP-1 in the presence and absence of DPPIV inhibitor and in the presence of high or low glucose. As is shown in FIG. 13, GRIS cells, stably co-transfected with a construct containing a nucleic acid encoding native GLP-1 and a construct having a nucleic acid encoding human furin, increased insulin production by RIN-5F cells compared to control U2OS cells. The parental U2OS was used to create this new GLP-1 producing cell line, however these GLP-1 producing GRIS cells do not encode insulin.

Figure 14:
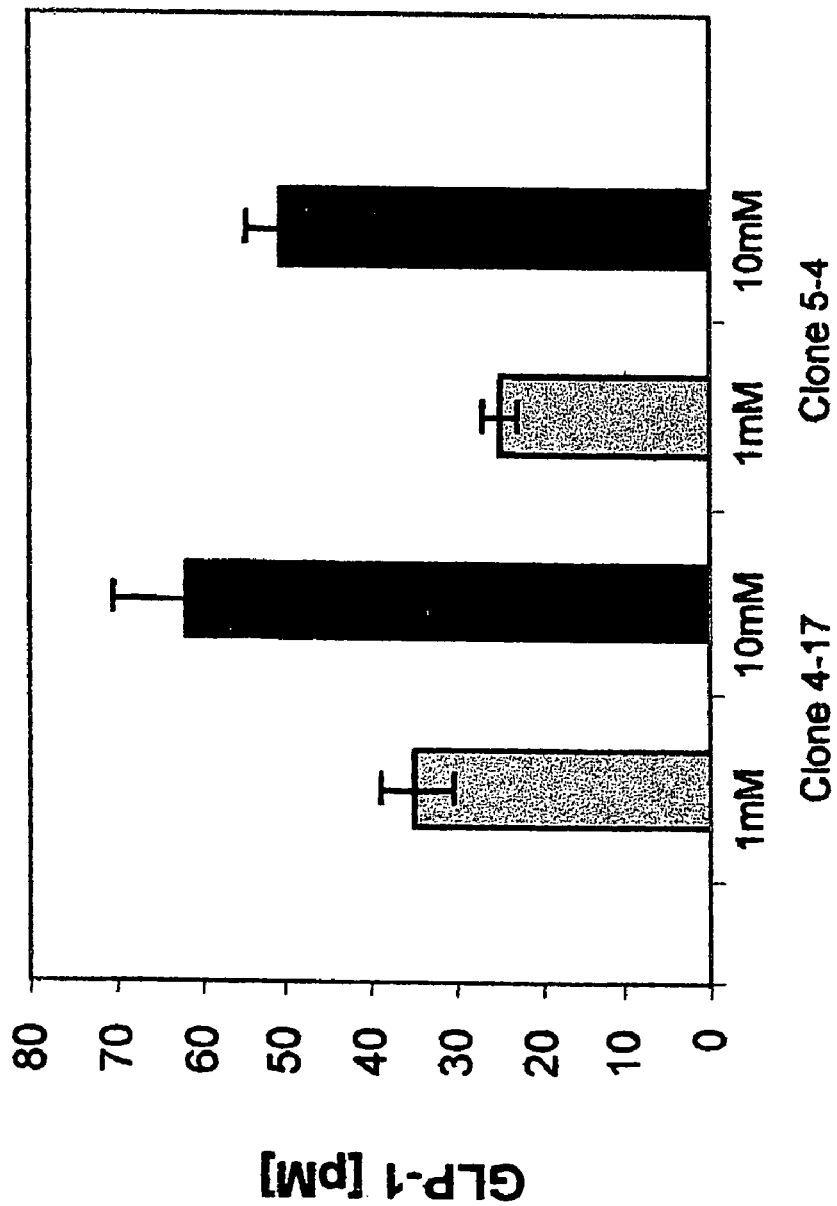
FIG. 14 illustrates the glucose-induced GLP-1 production from two clones designated 4-17 and 5-4 (which are arbitrary designations) which are stably transfected with a modified GLP-1 construct. The modified GLP-1 construct is stably transfected into glucose-responsive insulin secreting cells (GRIS cells), which are derived from U2OS cells. (U2OS are stably transfected with a construct comprising a nucleotide sequence encoding human proinsulin and a second construct encoding human furin, whose expression is under the control of a glucose-regulated TGF-alpha promoter.) The U2OS-derived GRIS cells transfected with the modified GLP-1 construct are a new GLP-1 producing cell line; these GLP-1 producing cells do not encode insulin. The modified GLP-1 construct comprises an optimized nucleic acid proinsulin leader sequence and a GLP-1 nucleic acid sequence with furin cleavage site; the expression the optimized sequence is driven by a CMV promoter. The construct encoding human furin is under the control of a glucose-regulated TGF-alpha promoter. Glucose activates expression of furin, which cleaves the optimized nucleic acid sequence at the furin cleavage site, thereby producing the encoded GLP-1. The presence of high glucose concentrations induced greater amounts of GLP-1 production in both clones compared to the amounts of GLP-1 expressed in the presence of low glucose concentrations.

FIG. 14 illustrates glucose-induced GLP-1 production from two clones, 4-17 and 5-4 stably transfected with the optimized GLP-1 construct. The GLP-1 construct was transfected into glucose-responsive insulin secreting cells (GRIS cells), which are derived from U2OS cells publicly available from the American Type Culture Collection (ATCC). GRIS cells, which are stably transfected with vectors expressing human furin under the control of glucose-regulated TGF-alpha promoter, co-express GLP-1 in the presence of high glucose, i.e., when the GLP-1 chimeric construct is cleaved by furin at the furin cleavable site. GLP-1 production was higher in clones in the presence of high glucose compared to clones incubated with low glucose. The two clones, 4-17 and 5-4, are the progeny of GRIS cells.

In a preferred embodiment of any of the herein described human cells, the human cell may be a 293T, HeLa, SHP77 or U2OS cell.

293T cells were transiently transfected with GLP-1 constructs to determine the level of production of GLP-1. FIG. 7 shows the amount (pM) of active and total GLP-1 produced using the GLP-1 constructs BI-1.2 (optimized) and 11.11 (native) in the transiently transfected 293T cells. The cells transfected with optimized GLP-1 produced higher amounts of GLP-1 than cells transfected with the native GLP-1.

Figure 8:
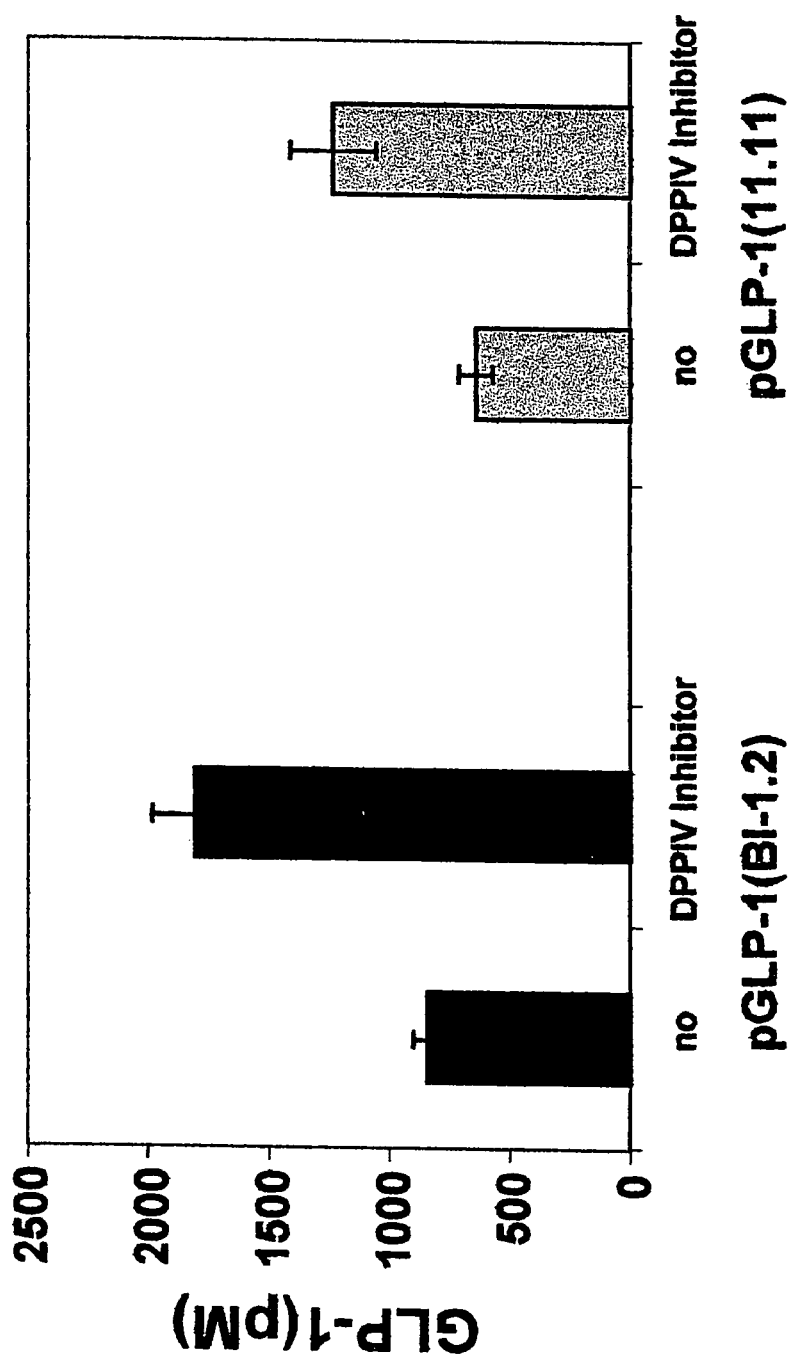
FIG. 8 shows the active GLP-1 production by transiently-transfected 293T cells in the presence of DPPIV inhibitor. DPPIV inhibitor inhibited degradation of active GLP-1 peptide produced by transfected cells.

When transiently transfected cells were incubated in the presence of DPPIV inhibitor, an inhibitor of the peptidase which cleaves GLP-1 at Ala2, more inhibition of degradation occurred than in the absence of the inhibitor, as illustrated in the bar graphs of FIG. 8.

This invention provides a method of producing human GLP-1 constitutively in an isolated human cell by stably transfecting the isolated human cells with (a) a recombinant expression vector comprising an isolated modified chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the nucleic acid sequence encoding GLP-1 constitutively, wherein the modified chimeric nucleic acid sequence is shown in SEQ ID NO:8 or (b) a recombinant expression vector comprising an isolated chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the nucleic acid sequence encoding GLP-1 constitutively, wherein the chimeric nucleic acid sequence is shown in SEQ ID NO:6. In an alternate embodiment of the method of producing human GLP-1 constitutively, the recombinant expression vector comprises an isolated modified chimeric nucleic acid sequence encoding a human pro-insulin leader, a glucagon-like peptide-1 (GLP-1)(7-36), a furin cleavable site between the human pro-insulin leader and the GLP-1(7-36), and a constitutive promoter which drives the expression of the nucleic acid sequence encoding GLP-1 constitutively. In this embodiment, the modified chimeric nucleic acid sequence is shorter than the sequence shown in SEQ ID NO:8, i.e., the sequence lacks the codon GGA, which encodes the final glycine (residue 37) found in GLP-1(7-37), and the encoded GLP-1 has the sequence of SEQ ID NO:10. In a further alternate embodiment, the recombinant expression vector comprises an isolated chimeric nucleic acid sequence encoding a human pro-insulin leader, a glucagon-like peptide-1 (GLP-1)(7-36), a furin cleavable site between the human pro-insulin leader and the GLP-1(7-36), and a constitutive promoter which drives the expression of the nucleic acid sequence encoding GLP-1 constitutively. In this latter embodiment, the isolated chimeric nucleic acid sequence is shorter than the sequence shown in SEQ ID NO:6, i.e., the sequence lacks the codon GGA and does not encode glycine (residue 37) found in GLP-1(7-37).

This invention also provides a method of producing human GLP-1 and insulin in a glucose-dependent manner in an isolated human cell, said method comprising: (a) stably transfecting the isolated human cell with (i) a recombinant expression vector comprising an isolated modified chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the nucleic acid sequence encoding GLP-1 constitutively, wherein the modified chimeric nucleic acid sequence is shown in SEQ ID NO:8, (ii) a second expression vector comprising an isolated nucleic acid sequence encoding human furin and a glucose-regulatable TGF-alpha promoter, wherein said promoter drives expression of the nucleotide sequence encoding human furin in a glucose-regulated manner, and (iii) a third expression vector comprising an isolated nucleic acid sequence encoding proinsulin, a furin cleavable site between the human pro-insulin leader sequence and insulin sequence and a constitutive promoter which drives the expression of the nucleic acid sequence encoding proinsulin constitutively; and (b) stimulating said cell with a glucose, wherein the concentration of the glucose is higher than an ambient concentration of glucose. In an alternate embodiment, modified chimeric nucleic acid sequence is shorter than the sequence shown in SEQ ID NO:8 by the lack of the codon GGA and does not encode glycine (residue 37) found in GLP-1(7-37). In the alternate provided embodiment, the encoded GLP-1 is GLP-1(7-36) shown in SEQ ID NO:10.

This invention further provides a method of producing human GLP-1 and insulin in a glucose-dependent manner in an isolated human cell, said method comprising: (a) stably transfecting the isolated human cell with (i) a recombinant expression vector comprising an isolated chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the isolated chimeric nucleic acid sequence constitutively, wherein the chimeric nucleic acid sequence is shown in SEQ ID NO:6, (ii) a second expression vector comprising an isolated nucleic acid sequence encoding human furin and a glucose-regulatable TGF-alpha promoter, wherein said promoter drives expression of the nucleotide sequence encoding human furin in a glucose-regulated manner, and (iii) a third expression vector comprising an isolated nucleic acid sequence encoding proinsulin, said proinsulin comprised of a human pro-insulin leader sequence, an insulin sequence and a furin cleavable site between the human pro-insulin leader sequence and the insulin sequence and a constitutive promoter which drives the expression of the nucleic acid sequence encoding proinsulin constitutively; and (b) stimulating said cell with a glucose, wherein the concentration of the glucose is higher than an ambient concentration of glucose. In an alternate embodiment, chimeric nucleic acid sequence is shorter than the sequence shown in SEQ ID NO:6 by the lack of the codon GGA and does not encode glycine (residue 37) found in GLP-1(7-37). In the alternate provided embodiment, the encoded GLP-1 is GLP-1(7-36) shown in SEQ ID NO:10.

An example of a cell which may be transfected with the above described expression vectors to produce GLP-1 or co-express GLP-1 and insulin are human cells such as 293T, HeLa, SHP77 or U2OS cell.

Figure 9:
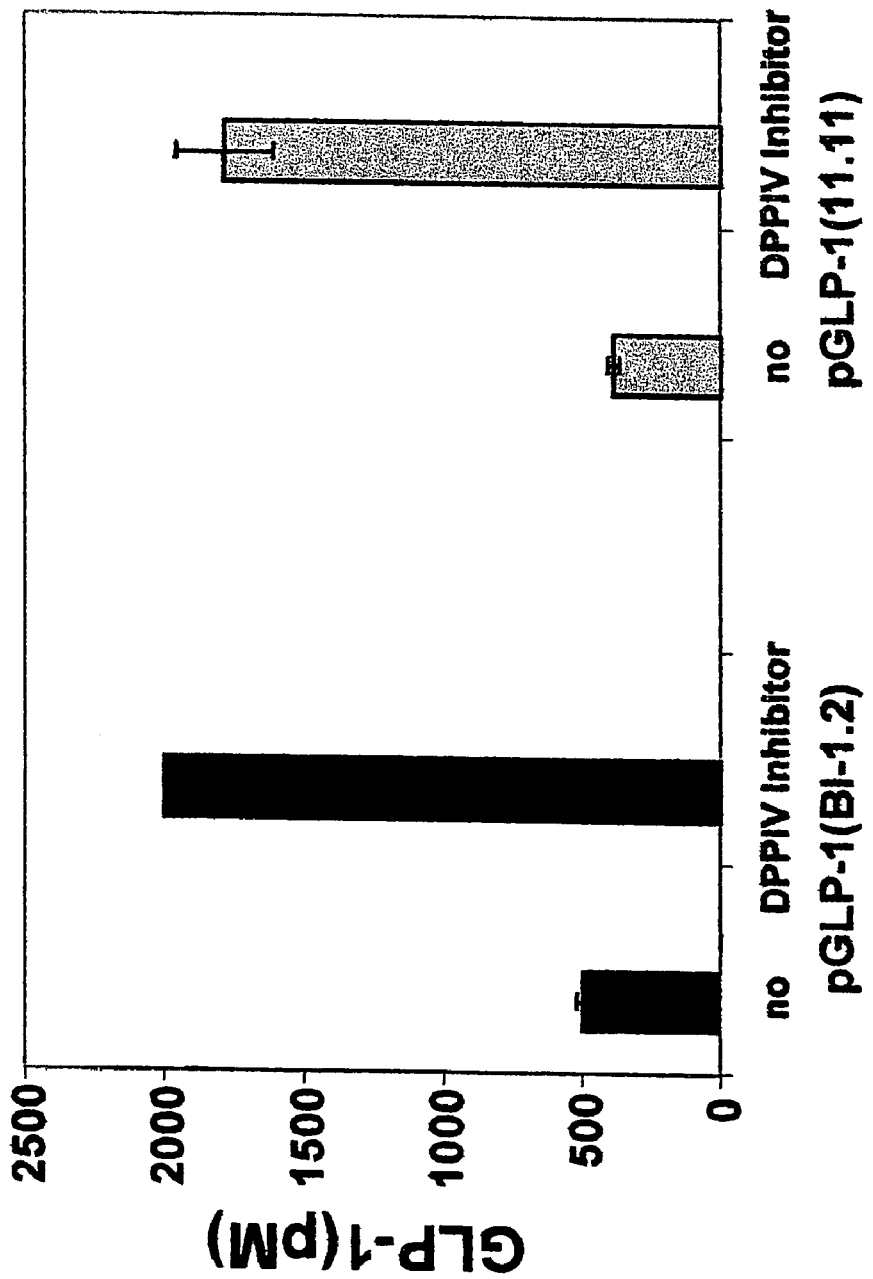
FIG. 9 illustrates the active GLP-1 production in transiently-transfected U2OS cells in the presence or absence of DPPIV inhibitor. DPPIV inhibitor inhibited degradation of active GLP-1 peptide produced by the transfected cells. Cells transfected with modified GLP-1 or native GLP-1 constructs produced comparable amounts of GLP-1.

The human osteosarcoma cell line, U2OS, was stably transfected with GLP-1 cDNA as described in Example 3. Transfected cells were tested for their ability to produce GLP-1 in the presence or absence of DPPIV inhibitor. As shown in FIG. 9, DPPIV inhibited degradation of active GLP-1 and comparable amounts of GLP-1 were produced by cells transfected with the optimized and the native GLP-1 constructs.

Figure 10:
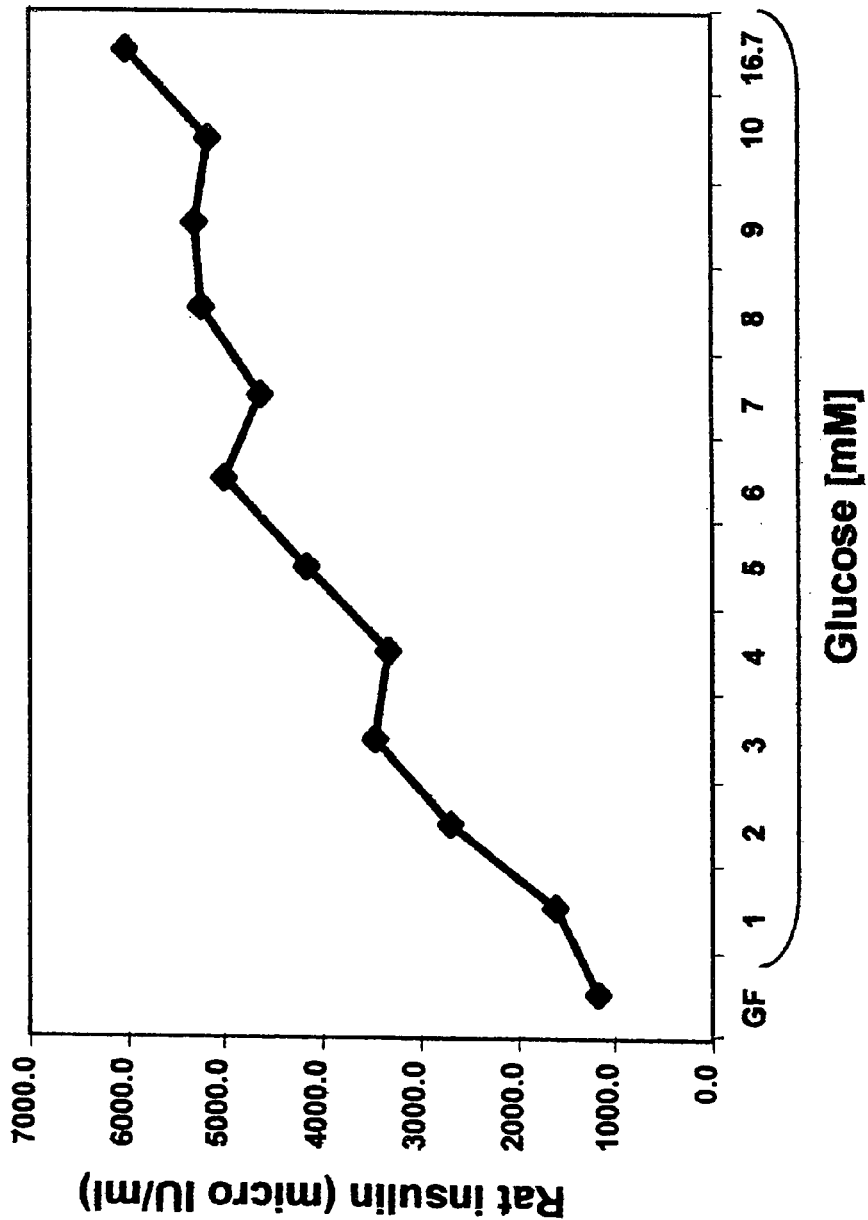
FIG. 10 graphically depicts the glucose-induced insulin production by RIN-5F cells. RIN-5F cells produced higher levels of insulin in response to glucose in a dose-dependent manner.
Figure 11:
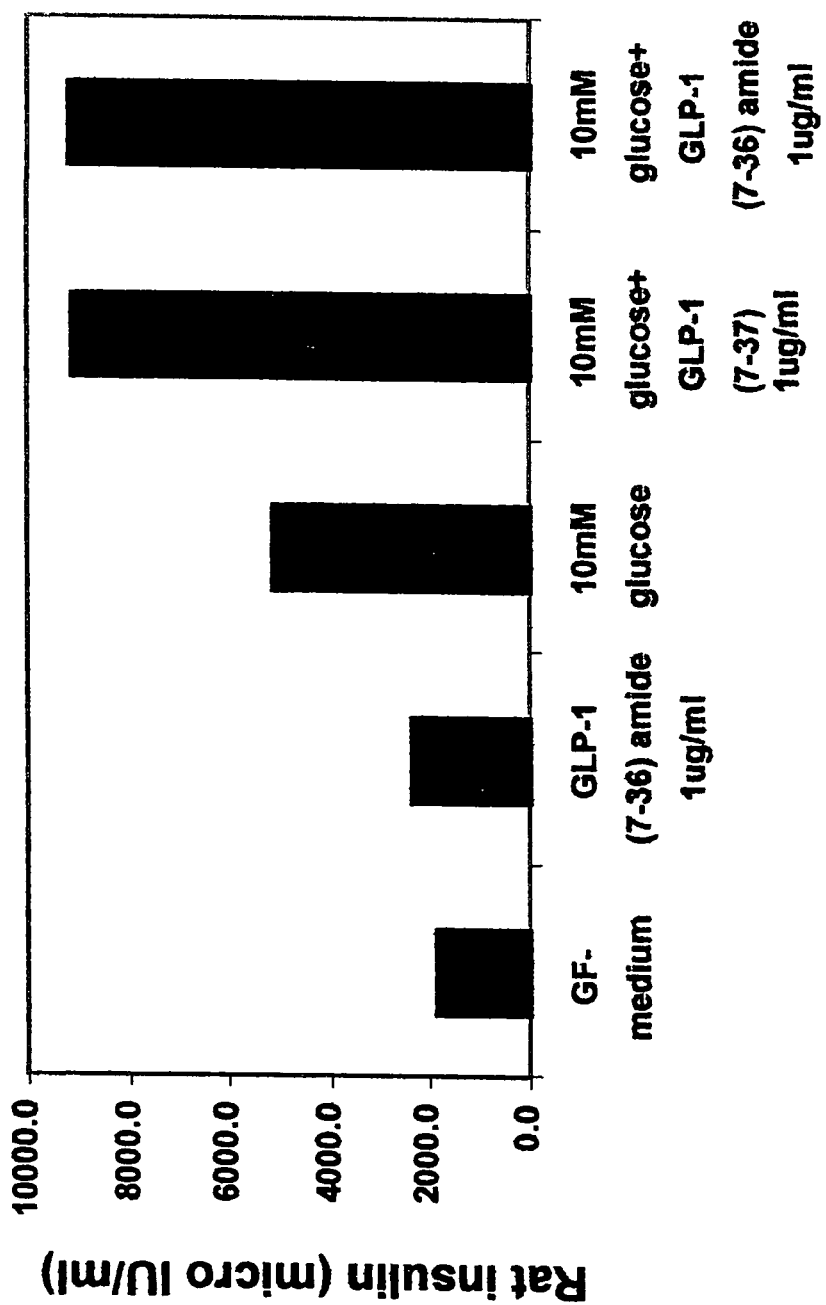
FIG. 11 shows the insulinotropic effect of GLP-1 on RIN-5F cells. GLP-1 augmented glucose-induced insulin production in RIN-5F cells.
Figure 12:
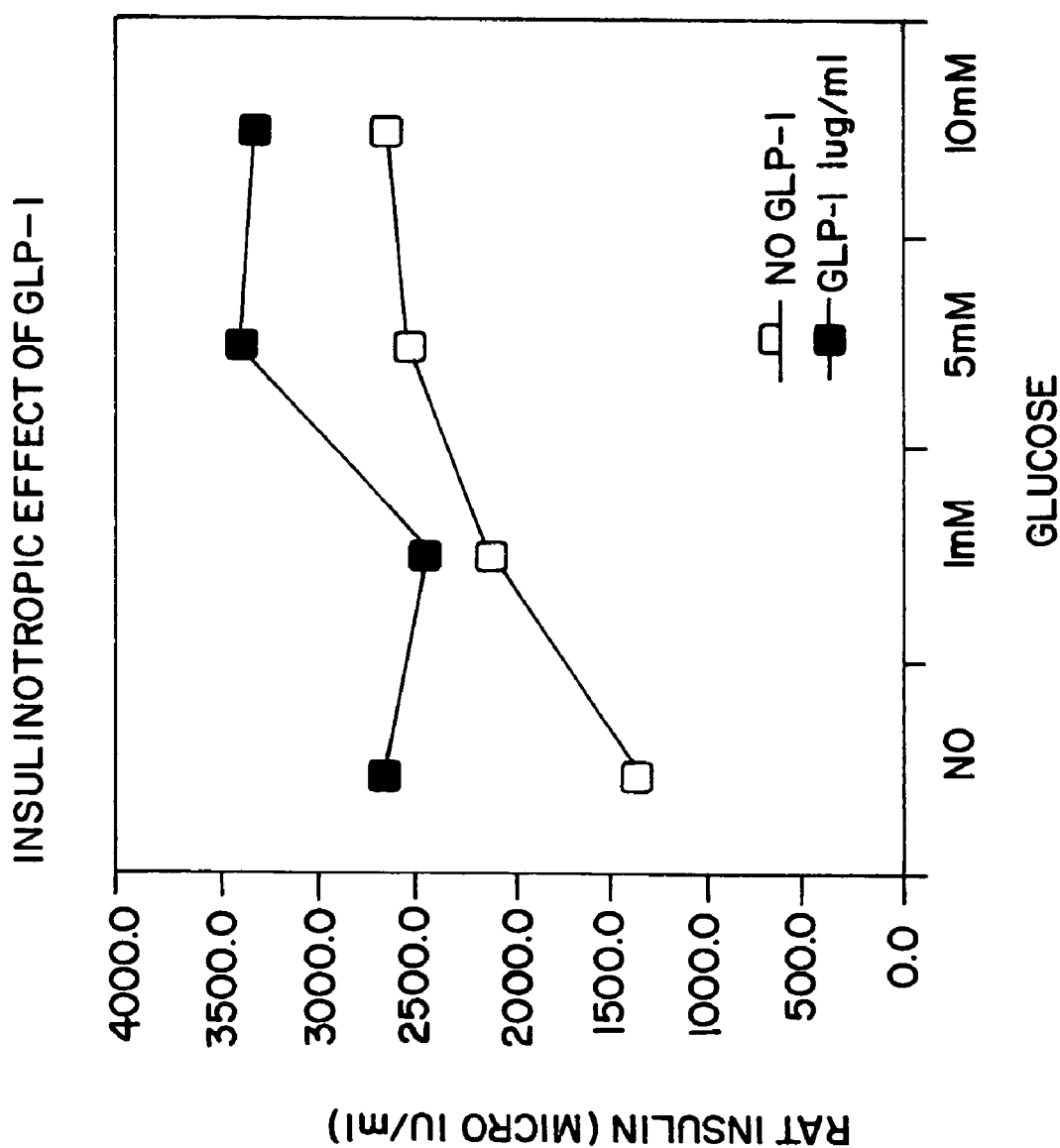
FIG. 12 illustrates the insulinotropic effect of GLP-1 at various glucose concentrations. Augmentation of insulin production is more evident at higher glucose concentration.

FIG. 10 illustrates the glucose-induced insulin production by RIN-5F cells, rat pancreatic islet tumor cells: higher levels of rat insulin were produced in response to glucose in a dose-dependent manner. RIN-5F cells were cultured with GLP-1 peptide, supernatants from GLP-1 transfected cells (GLP-1(7-37) or GLP-1(7-36) amide or control supernatants in the presence or absence of various concentrations of exogenously added glucose, as described in Example 5. Supernatants from these cultures were harvested after 24 hours for production of insulin. As shown in FIG. 11, the production of rat insulin increased dramatically in RIN-5F cells when treated with either GLP-(7-37) or GLP-1(7-36) amide in the presence of 10 mM of exogenously added glucose compared to cells cultured with medium, GLP-1(7-36) without glucose or glucose alone. FIG. 12 shows the insulinotropic effect of GLP-1 at various glucose concentrations. An increase in insulin production was found at higher glucose concentrations.

In preferred embodiment of each of the above-described methods of producing human GLP-1, the transfected human cell is implanted into a subject, wherein the subject has Type II diabetes. In another preferred embodiment, the transfected human cell is implanted into a subject in a immunoisolatory device, wherein the subject is prone to hyperglycemia or suffering from hyperglycemia, said subject being a non-diabetic overweight subject, a non-diabetic obese subject or a pre-diabetic subject. In any of the aforementioned embodiments, the implanted cells are in a biocompatible immunoisolatory device.

Figure 15:
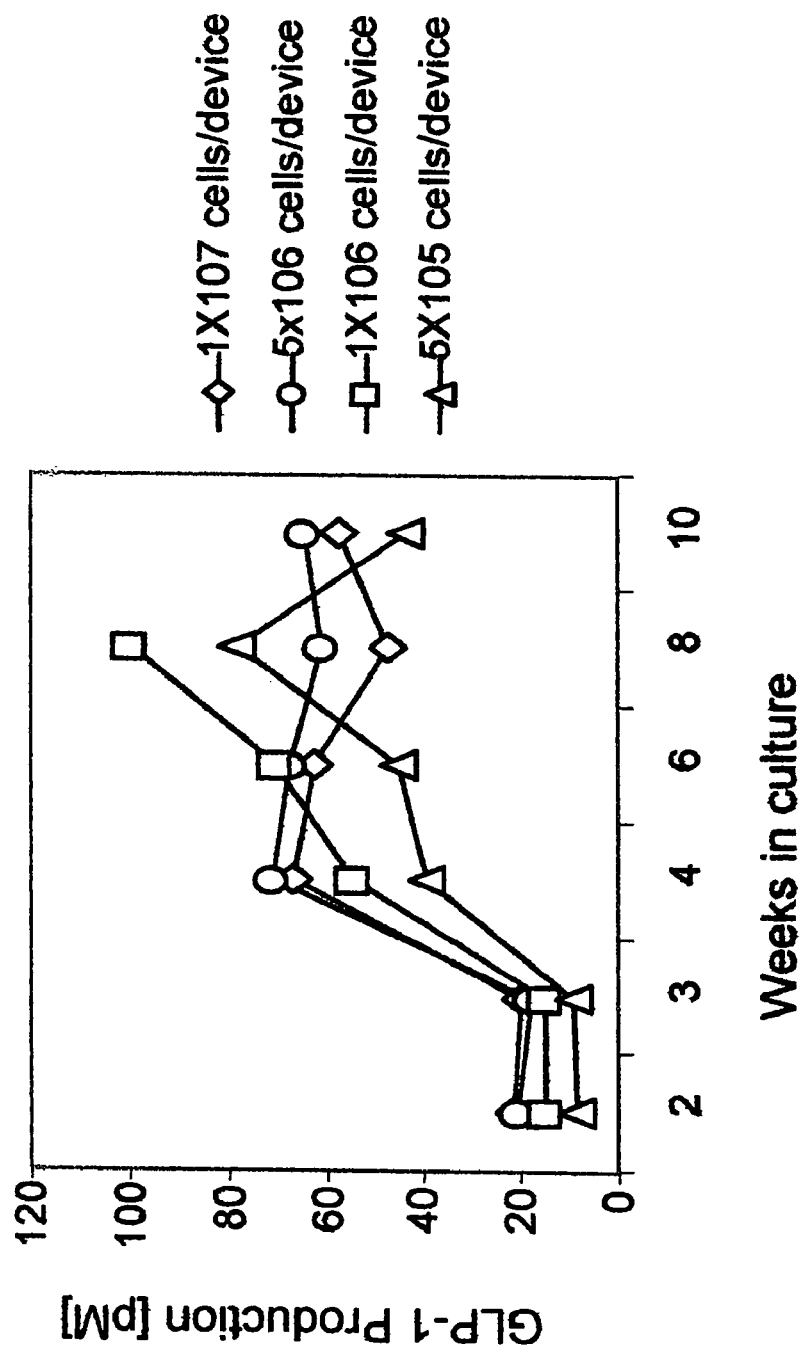
FIG. 15 graphically shows the constitutive production of GLP-1 by engineered cells grown in vitro in TheraCyte® devices for a 10 week period.

FIG. 15 illustrates the production of GLP-1 by engineered cells. GLP-1 constructs were transfected into U2O-25 cells and the transfected cells were grown in vitro in TheraCyte®. devices. All of the transfected cells produced GLP-1 for at least 8 weeks and three different concentrations of the cells produced GLP-1 for 10 weeks. These experiments support the viability and functionality of GLP-1 producing engineered cells which are implanted in an immunoisolatory device.

In another embodiment of the present invention, there is provided a method of treating a subject having Type II diabetes, said method comprising: implanting into the subject an immunoisolatory device, wherein said device comprises isolated human cells stably transfected with the (i) a recombinant expression vector comprising an isolated modified chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the modified chimeric nucleic acid sequence constitutively, wherein the modified chimeric nucleic acid sequence is shown in SEQ ID NO:8; (ii) a second expression vector comprising an isolated nucleic acid sequence encoding human furin and a glucose-regulatable TGF-alpha promoter, wherein said promoter drives expression of the nucleotide sequence encoding human furin in a glucose-regulated manner; and (iii) a third expression vector comprising an isolated nucleic acid sequence encoding proinsulin, a furin cleavable site between the human pro-insulin leader sequence and insulin sequence and a constitutive promoter which drives the expression of the nucleic acid sequence encoding proinsulin constitutively; wherein the isolated stably transfected cells express a therapeutically effective amount of GLP-1 and insulin in a glucose-dependent manner GLP-1 upon stimulation with a concentration of glucose in the blood of the subject, wherein the stimulating concentration of glucose is higher than an ambient concentration of glucose. In an alternate embodiment of this method of treatment, GLP-1(7-36), shown in SEQ ID NO:10, is encoded by the isolated modified chimeric nucleic acid sequence and produced by the above described expression vector. In the alternate embodiment, the isolated modified chimeric nucleic acid sequence is shorter than the sequence shown in SEQ ID NO:8 by the lack of the codon GGA and does not encode glycine (residue 37) found in GLP-1(7-37).

A further embodiment of the present invention is a method of treating a subject having Type II diabetes, said method comprising: implanting into the subject an immunoisolatory device, wherein said device comprises isolated human cells stably transfected with (i) a recombinant expression vector comprising an isolated chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the chimeric nucleic acid sequence constitutively, wherein the chimeric nucleic acid sequence is shown in SEQ ID NO:6; (ii) a second expression vector comprising an isolated nucleic acid sequence encoding human furin and a glucose-regulatable TGF-alpha promoter, wherein said promoter drives expression of the nucleotide sequence encoding human furin in a glucose-regulated manner; and (iii) a third expression vector comprising an isolated nucleic acid sequence encoding proinsulin, a furin cleavable site between the human pro-insulin leader sequence and insulin sequence and a constitutive promoter which drives the expression of the nucleic acid sequence encoding proinsulin constitutively; wherein the isolated stably transfected human cells express a therapeutically effective amount of GLP-1 and insulin in a glucose-dependent manner GLP-1 upon stimulation with a concentration of glucose in the blood of the subject, wherein the stimulating concentration of glucose is higher than an ambient concentration of glucose. In another embodiment of this method of treatment, GLP-1(7-36), shown in SEQ ID NO:10, is encoded by the isolated chimeric nucleic acid sequence and produced by above described expression vector. In the alternate embodiment, the isolated chimeric nucleic acid sequence is shorter than the sequence shown in SEQ ID NO:6 by the lack of the codon GGA and does not encode glycine (residue 37) found in GLP-1(7-37).

A further embodiment of the present invention is a method of treating a subject prone to hyperglycemia or suffering from hyperglycemia, said method comprising: implanting into the subject an immunoisolatory device, wherein said device comprises isolated human cells stably transfected with (i) a recombinant expression vector comprising an isolated modified chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the nucleic acid sequence encoding GLP-1 constitutively, wherein the modified chimeric nucleic acid sequence is shown in SEQ ID NO:8, (ii) a second expression vector comprising an isolated nucleic acid sequence encoding human furin and a glucose-regulatable TGF-alpha promoter, wherein said promoter drives expression of the nucleotide sequence encoding human furin in a glucose-regulated manner, and (iii) a third expression vector comprising an isolated nucleic acid sequence encoding proinsulin, a furin cleavable site between the human pro-insulin leader sequence and insulin sequence and a constitutive promoter which drives the expression of the nucleic acid sequence encoding proinsulin constitutively; wherein the isolated stably transfected cells express a therapeutically effective amount of GLP-1 and insulin in a glucose-dependent manner upon stimulation with a concentration of glucose in the blood of the subject, wherein a stimulating concentration of glucose is higher than an ambient concentration of glucose, thereby reducing glucose blood level.

Alternatively, the present invention provides a method of treating a subject prone to hyperglycemia or suffering from hyperglycemia, said method comprising: implanting into the subject an immunoisolatory device, wherein said device comprises isolated human cells stably transfected with (i) a recombinant expression vector comprising an isolated chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the chimeric nucleic acid sequence constitutively, wherein the chimeric nucleic acid sequence is shown in SEQ ID NO:6, (ii) a second expression vector comprising an isolated nucleic acid sequence encoding human furin and a glucose-regulatable TGF-alpha promoter, wherein said promoter drives expression of the nucleotide sequence encoding human furin in a glucose-regulated manner, and (iii) a third expression vector comprising an isolated nucleic acid sequence encoding proinsulin, a furin cleavable site between the human pro-insulin leader sequence and insulin sequence and a constitutive promoter which drives the expression of the nucleic acid sequence encoding proinsulin constitutively; wherein the isolated stably transfected human cells express a therapeutically effective amount of GLP-1 and insulin in a glucose-dependent manner GLP-1 upon stimulation with a concentration of glucose in the blood of the subject, wherein the stimulating concentration of glucose is higher than an ambient concentration of glucose, thereby reducing glucose blood level.

In another embodiment of the above-described methods of treatment a subject prone to hyperglycemia or suffering from hyperglycemia, the respective recombinant expression vector comprises an isolated modified chimeric nucleic acid sequence which encodes GLP-1(7-36) and produces GLP-1 (7-36), shown in SEQ ID NO:10, or the recombinant expression vector comprises an isolated chimeric nucleic acid sequence encoding GLP-1(7-36). In one of these alternate embodiments, GLP-1(7-36) is encoded by an isolated modified chimeric nucleic acid sequence that is shorter than SEQ ID NO:8, i.e., lacks the codon GGA and does not encode glycine (residue 37) encoded by this codon in GLP-1(7-37). In another of these alternate embodiments, GLP-1(7-36) is encoded by an isolated chimeric nucleic acid sequence that is shorter than SEQ ID NO:6, i.e., lacks the codon GGA and the expressed peptide lacks the glycine (residue 37) found in GLP-1(7-37).

In another embodiment, there is provided a method of reducing weight in a subject, said method comprising: implanting into the subject an immunoisolatory device, wherein said device comprises isolated human cells stably transfected with (i) a recombinant expression vector comprising an isolated modified chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the nucleic acid sequence encoding GLP-1 constitutively, wherein the modified chimeric nucleic acid sequence is shown in SEQ ID NO:8, (ii) a second expression vector comprising an isolated nucleic acid sequence encoding human furin and a glucose-regulatable TGF-alpha promoter, wherein said promoter drives expression of the nucleotide sequence encoding human furin in a glucose-regulated manner, and (iii) a third expression vector comprising an isolated nucleic acid sequence encoding proinsulin, a furin cleavable site between the human pro-insulin leader sequence and insulin sequence and a constitutive promoter which drives the expression of the nucleic acid sequence encoding proinsulin constitutively; wherein the isolated stably transfected cells express a therapeutically effective amount of GLP-1 and insulin in a glucose-dependent manner upon stimulation with a concentration of glucose in the blood of the subject, wherein the stimulating concentration of glucose is higher than an ambient concentration of glucose, wherein the GLP-1 and insulin expression reduces the weight of the subject. In another embodiment, the recombinant expression vector comprises an isolated modified chimeric nucleic acid sequence encoding a human pro-insulin leader, a glucagon-like peptide-1 (GLP-1)(7-36), a furin cleavable site between the human pro-insulin leader and the GLP-1(7-36), and a constitutive promoter which drives the expression of the nucleic acid sequence encoding GLP-1(7-36) constitutively, i.e., the nucleic acid sequence is shorter than SEQ ID NO:8 by the lack of the codon GGA encoding glycine (residue 37 in GLP-1(7-37)) and the encoded GLP-1 is GLP-1(7-36), shown in SEQ ID NO:10.

There is provided herein a method of reducing weight in a subject, said method comprising: wherein said device comprises isolated human cells stably transfected (i) a recombinant expression vector comprising an isolated chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the chimeric nucleic acid sequence constitutively, wherein the chimeric nucleic acid sequence is shown in SEQ ID NO:6, (ii) a second expression vector comprising an isolated nucleic acid sequence encoding human furin and a glucose-regulatable TGF-alpha promoter, wherein said promoter drives expression of the nucleotide sequence encoding human furin in a glucose-regulated manner, and (iii) a third expression vector comprising an isolated nucleic acid sequence encoding proinsulin, a furin cleavable site between the human pro-insulin leader sequence and insulin sequence and a constitutive promoter which drives the expression of the nucleic acid sequence encoding proinsulin constitutively; wherein the isolated stably transfected cells express a therapeutically effective amount of GLP-1 and insulin in a glucose-dependent manner upon stimulation with a concentration of glucose in the blood of the subject, wherein the stimulating concentration of glucose is higher than an ambient concentration of glucose, wherein the GLP-1 and insulin expression reduces the weight of the subject. In another embodiment, the recombinant expression vector comprises an isolated chimeric nucleic acid sequence encodes a human pro-insulin leader, a glucagon-like peptide-1 (GLP-1)(7-36), a furin cleavable site between the human pro-insulin leader and the GLP-1(7-36), and a constitutive promoter which drives the expression of the nucleic acid sequence encoding GLP-1(7-36) constitutively, i.e., the nucleic acid sequence is shorter than SEQ ID NO:6 by the lack of the codon GGA encoding glycine (residue 37 in GLP-1(7-37)) and the encoded GLP-1 is GLP-1(7-36), shown in SEQ ID NO:10.

In further embodiments of the present invention, provided are methods of treating a subject having Type II diabetes, treating a subject prone to hyperglycemia or suffering from hyperglycemia, and reducing weight in a subject, said methods comprising implanting into the subject an immunoisolatory device containing constitutive GLP-1 producing cells. The cells produce a therapeutically effective amount of GLP-1 constitutively.

In an embodiment, provided is a method of treating a subject having Type II diabetes, said method comprising: implanting into the subject an immunoisolatory device, wherein said device comprises isolated human cells stably transfected with (a) a recombinant expression vector comprising an isolated modified chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the nucleic acid sequence encoding GLP-1 constitutively, wherein the modified chimeric nucleic acid sequence is shown in SEQ ID NO:8 or (b) a recombinant expression vector comprising an isolated chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the chimeric nucleic acid sequence constitutively, wherein the chimeric nucleic acid sequence is shown in SEQ ID NO:6, wherein said cell produces endogenous furin. In further alternate embodiments, the expressed GLP-1 is GLP-1 (7-36) rather than GLP-1(7-37). In the respective alternate embodiments, the modified chimeric nucleic acid sequence is shorter than SEQ ID NO:8 and the chimeric nucleic acid sequence is shorter than SEQ ID NO:6, respectively, by the lack of the codon GGA encoding glycine (residue 37 in GLP-1(7-37)) and thus, the encoded GLP-1 is GLP-1(7-36), shown in SEQ ID NO:10.

In another embodiment, the invention provides a method of treating a subject prone to hyperglycemia or suffering from hyperglycemia, said method comprising implanting into the subject an immunoisolatory device, wherein said device comprises isolated human cells stably transfected with (a) a recombinant expression vector comprising an isolated modified chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the nucleic acid sequence encoding GLP-1 constitutively, wherein the modified chimeric nucleic acid sequence is shown in SEQ ID NO:8 or (b) a recombinant expression vector comprising an isolated chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the chimeric nucleic acid sequence constitutively, wherein the chimeric nucleic acid sequence is shown in SEQ ID NO:6, wherein said cell produces endogenous furin. In further embodiments, the GLP-1 is GLP-1 (7-36) rather than GLP-1 (7-37). In such respective alternate embodiments, the modified chimeric nucleic acid sequence is shorter than SEQ ID NO:8 and the chimeric nucleic acid sequence is shorter than SEQ ID NO:6, respectively, by the lack of the codon GGA encoding glycine (residue 37 in GLP-1(7-37)) and thus, the encoded GLP-1 is GLP-1(7-36), shown in SEQ ID NO:10.

In another embodiment of the invention, there is provided a method of reducing weight in a subject, said method comprising implanting into the subject an immunoisolatory device, wherein said device comprises isolated human cells stably transfected with (a) a recombinant expression vector comprising an isolated modified chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the nucleic acid sequence encoding GLP-1 constitutively, wherein the modified chimeric nucleic acid sequence is shown in SEQ ID NO:8 or (b) a recombinant expression vector comprising an isolated chimeric nucleic acid sequence encoding a human pro-insulin leader, a glucagon-like peptide-1 (GLP-1)(7-37), a furin cleavable site between the human pro-insulin leader and the GLP-1(7-37), and a constitutive promoter which drives the expression of the chimeric nucleic acid sequence constitutively, wherein the chimeric nucleic acid sequence is shown in SEQ ID NO:6, wherein said cell produces endogenous furin. In a further embodiment, the GLP-1 is GLP-1 (7-36) rather than GLP-1(7-37). In the respective alternate embodiments, the modified chimeric nucleic acid sequence is shorter than SEQ ID NO:8 and the chimeric nucleic acid sequence is shorter than SEQ ID NO:6, respectively, by the lack of the codon GGA encoding glycine (residue 37 in GLP-1(7-37)) and thus, the encoded GLP-1 is GLP-1(7-36), shown in SEQ ID NO:10. The effect of the insulin production is a reduction in the weight of the subject.

In embodiments of the above-described methods of treating Type II diabetes, the Type II diabetic subject may be treated concurrently with (a) a diet, (b) metformin, sulfonylurea, or exenatide, or (c) a combination thereof. In embodiments of the methods of treatment of a non-diabetic subject having hyperglycemia, the subject may be an overweight subject, a non-diabetic obese subject or a pre-diabetic.

EXAMPLE 1

GLP-1 Constructs

In order to obtain a biologically active form of secreted GLP-1 from genetically engineered cells, the following strategy is used to generate the GLP-1 nucleic acid constructs. The active GLP-1(7-37) peptide is comprised of 31 residues, accordingly the nucleotide sequence corresponding to these residues is conveniently split in half to generate two separate fragments viz., N-terminal and C-terminal fragments as shown in FIG. 3-B. Complementary oligonucleotides corresponding to these amino acids are synthesized with the modifications listed below. Sequences of the oligonucleotides are listed in SEQ ID NO:1, SEQ ID NO:2, SEQ ID NO:3 and SEQ ID NO:4.

An XhoI restriction site is added at the split site, without altering the amino acid sequence. A furin cleavage site (RQK'R) and the Kozak sequence and the bases consistent with the overhang of NheI restriction site are added to the 5' end of the N-terminal fragment as shown in FIGS. 3-B and C. Bases consistent with the overhang of BamHI are added to the 3' end of the C-terminal fragment as illustrated in FIGS. 3-B and C. All oligonucleotides are phosphorylated at the 5' end.

Complementary oligonucleotides of N-terminal and C-terminal fragments are annealed and subcloned separately into pCDNA3.1 expression vector using NheI and XhoI cloning sites for the N-terminal fragment and using XhoI and BamHI sites for the C-terminal fragment.

The C-terminal fragment is excised using XhoI and BamHI and subcloned downstream of the N-terminal fragment using these same restriction sites as shown in FIG. 3-C.

The human proinsulin leader sequence is PCR-amplified and subcloned just upstream of the furin cleavage site as shown in FIG. 3-D. The chimeric protein and nucleotide sequence encoding said chimeric protein containing the pro-insulin leader sequence, furin cleavage site and native GLP-1 are listed in SEQ ID NO: 5 and SEQ. ID NO:6, respectively. The vector map of this chimeric nucleic acid construct is shown in FIG. 4.

Modification of Proinsulin Leader/GLP-1 Sequence by Codon Usage

The chimeric protein sequence containing the human pro-insulin leader sequence, furin cleavage site and GLP-1 sequence (SEQ. ID 7) is used for synthesis of a modified nucleotide sequence (SEQ ID NO:8), which encodes a modified chimeric "human proinsulin leader-furin cleavage site-GLP-1" sequence (SEQ. ID NO: 7). This modified nucleotide sequence is synthesized by commercial sources. For example, the modified nucleic acid sequence of SEQ ID NO:8 was made by a company called Aptagen, Inc., which used its own algorithm based on codon usage to arrive at the sequence. The modified nucleotide sequence encoding pro-insulin leader/furin cleavage site/GLP-1 was subcloned into a pCIneo eukaryotic expression vector as illustrated in FIG. 5.

A sequence alignment of the chimeric nucleotide sequence containing native GLP-1 (bottom) (SEQ ID NO: 24) and the chimeric nucleotide sequence containing the optimized GLP-1 sequence (top) (SEQ ID NO: 25), as well as the respectively encoded amino acid sequences (SEQ ID NOs: 5 and 7) is shown in FIG. 6. Nucleotides 13-210 of SEQ ID NO: 24 are identical to SEQ ID NO: 6 and encode SEQ ID NO: 5, and nucleotides 16-195 of SEQ ID NO: 25 are identical to SEQ ID NO: 8 and encode SEQ ID NO: 7. The modified chimeric nucleic acid sequence, i.e., in which the codons for each amino acid residue are the preferred codons based on an algorithm program, encodes the modified chimeric amino acid sequence for proinsulin leader/furin cleavage site/GLP-1 in which amino acids LLATMG [in SEQ ID NO:5] upstream of the furin cleavage site have been removed.

EXAMPLE 2

Assessment of GLP-1 Secreted in Transiently Transfected Cells

Various human cell lines (293T, HeLa, SHP77, U2OS) are transiently transfected with GLP-1 constructs to assess production of GLP-1 in the culture medium. The transfections are performed as follows.

Cells are plated at $2.5 \times 10^5$ cells/60 mm dish in 4.0 ml culture medium. The cells are allowed to adhere overnight. The cells are 40-60% confluent after the overnight culture. The medium is removed from the cells so that there is 1.5 ml remaining in the plate.

In a sterile microtube 1 µg DNA is added into a total of 150 µl DNA-condensation buffer (EC buffer, Qiagen Effectene transfection kit). Enhancer solution (8 µl 1) is added into the DNA/EC buffer, vortexed for 1 second and incubated for 2-5 minutes at room temperature. 25 µl Effectene is added into each tube and vortexed for 10 seconds. The tubes are allowed to sit at room temperature for 5-10 min. The transfection mixture is diluted with 1.0 ml media and added drop wise over cells. The dishes are swirled and the cells are returned to 37°

C./5% $CO_2$. The complexes, i.e., transfected cells, are removed at 4 hours, and the cells are fed with 2.0 ml fresh media. Supernatants are collected at 24 and 48 hours to assess GLP-1 secretion. Active GLP-1 is measured using Active GLP-1 ELISA kit (LINCO Diagnostic Services, Inc.), whereas total GLP-1 is detected by radioimmunoassay (LINCO Diagnostic Services, Inc).

FIG. 7 illustrates the active and total GLP-1 amounts which transiently-transfected 293T cells produce. Cells transfected with modified GLP-1 constructs (GLP-1 BI-1.2) produce higher amount of GLP-1 than the cells transfected with native GLP-1 constructs (GLP-1 11.11).

The transiently-transfected 293T cells are tested for the production of active GLP-1 in the presence of DPPIV inhibitor. FIG. 8 shows that the DPPIV inhibitor inhibits degradation of active GLP-1 peptide produced by cells transfected with either the native GLP-1 (GLP-1 11.11) or modified GLP-1 construct (GLP-1 BI-1.2). The cells transfected with the modified constructs produce more active GLP-1 than cells transfected with the native GLP-1 construct with or without the DPPIV inhibitor.

EXAMPLE 3

Engineering of Human U2OS Cells to Produce GLP-1

Human osteosarcoma cell line U2OS, available from the ATCC, is stably transfected with GLP-1 cDNA using the following protocol. The vector is linearized with BglII. The cells are co-transfected with pCDNA-huFurin expressing human furin. pCDNA-huFurin is linearized using MfeI. U2OS cells are seeded in 10-cm plates the day before at $2.5 \times 10^5$ per plate. The cells are transfected using calcium phosphate (Promega).

Three days post-transfection, medium is supplemented with 1000 μg/ml Geneticin. Once colonies are evident, cells are expanded in 6-well plates and tested for GLP-1 expression by active GLP-1 ELISA kit (Linco Diagnostic Services, Inc.). Cell populations producing high levels of GLP-1 are further cloned by limiting dilution at 1 cell/well. The clones are tested for their ability to produce GLP-1 in the presence and absence of DPPIV inhibitor.

The production of active GLP-1 in U2OS cells transiently transfected with native GLP-1 or modified GLP-1 (See Example 2) in the presence or absence of DPPIV inhibitor is shown in FIG. 9. DPPIV inhibitor inhibits degradation of active GLP-1 peptide produced by both native GLP-1 transfected cells and modified GLP-1 transfected cells. Cells transfected with modified or native GLP-1 constructs produce comparable amounts of GLP-1.

EXAMPLE 4

Engineering of Human Cells to Produce Glucose-Regulated Production of GLP-1

Cells are produced by stably transfecting glucose-responsive insulin secreting cells (GRIS cells) with the GLP-1 cDNA. GRIS cell clones 4-17 and 5-4 as shown in FIG. 14. GRIS cells are derived originally from U2OS cells by stable transfection with proinsulin and human furin under the control of glucose-regulatable TGF-alpha promoter by methods described in U.S. Patent Application Publication No. US2003/0032144 A1, published Feb. 13, 2003, now U.S. Pat. No. 7,045,346, which are incorporated herein by reference in their entirety. These U2OS cells are neomycin and hygromycin resistance. Therefore, the GLP-1 construct generated above is subcloned into the pCDNA3.1-Zeo vector to use Zeocin as a selectable marker for GLP-1 producing cells. For stable transfection of GRIS cells with pCDNA3.1(−)Zeo the following protocol is used.

The vector is linearized with PvuI. Transfections are also performed using non-linearized vector. GRIS cells are seeded in 10-cm plates the day before at $2 \times 10^6$, $4 \times 10^6$, $6 \times 10^6$, $8 \times 10^6$ or $10^6$ per plate. The cells are transfected using calcium phosphate (Promega).

Two days post-transfection, the medium is supplemented with 100 μg/ml Zeocin (no other drugs) and increased to 200 μg/μl Zeocin after 1 week. Once colonies are evident, cells are expanded and tested for GLP-1 expression using active GLP-1 ELISA kit (Linco Diagnostic, Inc.). Populations producing high levels of GLP-1 are further cloned by limiting dilution. The clones are tested in the presence or absence of DPPIV inhibitor, and in the presence of high or low glucose for production of GLP-1.

FIG. 9 illustrates the production of active GLP-1 in U2OS cells transiently transfected with modified GLP-1 constructs compared to cells transiently transfected with native GLP-1 constructs in the presence or absence of DPPIV inhibitor. Degradation of active GLP-1 peptide is inhibited by DPPIV inhibitor in both the native GLP-1-construct transfected cells and the modified GLP-1 -construct transfected cells. Cells transiently transfected with either the modified or the native GLP-1 constructs produce comparable amounts of GLP-1.

Glucose-induced GLP-1 production by two GRIS cell clones, viz 4-17 and 5-4, both of which are stably transfected with the herein described modified GLP-1 construct, is shown in FIG. 14. Both clones express and secrete GLP1 in a glucose regulated manner as exemplified by expression of greater amounts of GLP-1 when incubated with a high glucose concentration than when they are incubated with a low glucose concentration.

EXAMPLE 5

Insulinotropic Effect of GLP-1 on Insulin Production by RIN-5F Cells

RIN-5F cells are plated in a 6-well plate at $5 \times 10^5$/well in 5 ml complete medium (or a 24-well plate at $1 \times 10^5$/well in 2 ml complete medium) and cultured overnight for attachment to wells. Complete medium is replaced with 2 ml of glucose-free medium (Glucose-free RPMI+10% dialyzed FBS). Cells are incubated for at least 6 hrs at 37° C. in glucose-free medium. Cells are washed 1× with glucose-free medium. The cultures are fed with glucose-free RPMI+10% dialyzed FBS and further supplemented either with GLP-1 peptide, supernatants from GLP-1 (7-37)-transfected cells and GLP-1(7-36) amide-transfected cells or control supernatants in the presence or absence of various concentrations of exogenously added glucose. Final volume is adjusted to 2 ml. Supernatants from these cultures are harvested after 24 hrs for production of RAT insulin.

FIG. 10 illustrates the glucose-induced insulin production by RIN-5F cells. The insulin production is generally dose-dependent, i.e., more insulin is produced in higher concentrations of glucose.

FIG. 11 shows the insulinotropic effect of commercially obtained GLP-1 on RIN-5F cells under the following incubations conditions: glucose free (GF) medium, GLP-1(7-36) amide, glucose, glucose plus GLP-1(7-36)amide and glucose plus GLP-1(7-36). GLP-1, both (7-36) amide or (7-37), in the presence of high glucose (10 mM) augments glucose-induced insulin production in RIN-5F cells significantly over the amount of insulin produced by RIN-5F cells fed with medium, GLP(7-36) amide or glucose alone.

FIG. 12 graphically depicts rat insulin production by RIN-5F cells in various concentrations of glucose with or without GLP-1 (7-37). The GLP-1(7-37), which is commercially available, shows an insulinotropic effect.

Rat RIN-5F cells are tested for the production of insulin in the presence of differing concentrations of glucose and GLP-1 (7-37) at a fixed concentration of 1 micro g/ml).

GLP-1 alone (no glucose) showed some induction of insulin production by RIN5F cells, which did not change at low glucose (1 mM). At high glucose concentrations (5 and 10 mM) insulinotropic effect of GLP-1 is observed.

It should be understood that some modification, alteration and substitution is anticipated and expected from those skilled in the art without departing from the teachings of the invention. Accordingly, it is appropriate that the following claims be construed broadly and in a manner consistent with the scope and spirit of the invention.

What is claimed is:

1. An isolated polynucleotide whose nucleotide sequence is shown in SEQ ID NO:20 and is modified from SEQ ID NO:6 in that one or more codons of SEQ ID NO:6 encoding the amino acid sequence LLATMG is replaced with a codon selected from the group consisting of GCA/C/G/T, AAC/T, GAC/T, TGC/T, GAC/T, GAA/G, TTC/T, GGA/C/G/T, CAC/T, ATA/C/T, AAA/G, CTA/C/G/T, TTA/G, ATG, AAC/T, CCA/C/G/T, CAA/G, AGA/G, CGA/C/G/T, AGC/T, TCA/C/G/T, ACA/C/G/T, GTA/C/G/T, TGG, TAC/T, CAA/G and GAA/G, wherein said modified, isolated polynucleotide encodes a human pro-insulin leader, a glucagon-like peptide-1 (GLP-1), and a furin cleavable site between the human pro-insulin leader and the GLP-1.

2. An isolated polynucleotide having the nucleotide sequence shown in SEQ ID NO:6, wherein said nucleotide sequence encodes a human pro-insulin leader, a glucagon-like peptide-1 (GLP-1), and a furin cleavable site between the human pro-insulin leader and the GLP-1.

3. An isolated chimeric polypeptide having the amino acid sequence shown in SEQ ID NO:5.

4. An isolated chimeric polypeptide having the amino acid sequence shown in SEQ ID NO:21 and is modified from SEQ ID NO:5 in that one or more amino acids of the amino acid sequence LLATMG of SEQ ID NO:5 is replaced with an amino acid selected from the group consisting of A, R, N, D, C, E, Q, G, H, I, L, K, M, F, P, S, T, W, Y and V, respectively.

5. A recombinant expression vector comprising a constitutive promoter which drives the expression of the nucleotide sequence of claim 1 encoding a human pro-insulin leader, a glucagon-like peptide-1 (GLP-1)(7-37), and a furin cleavable site between the human pro-insulin leader and the (GLP-1)(7-37).

6. An isolated human cell stably transfected with the recombinant expression vector of claim 5, wherein said cell produces furin endogenously.

7. The recombinant expression vector of claim 5, which further comprises a glucose-regulatable TGF-alpha promoter that drives the expression of a nucleic acid sequence encoding human furin.

8. A method of producing human GLP-1 constitutively in an isolated human cell, said method comprising: stably transfecting the isolated human cell with the recombinant expression vector of claim 5, wherein said cell produces endogenous furin.

9. A method of treating a subject having Type II diabetes, said method comprising implanting into the subject an immunoisolatory device comprising isolated human cells stably transfected with the recombinant expression vector of claim 5, wherein said isolated human cells produce endogenous furin.

10. A method of treating a subject prone to hyperglycemia or suffering from hyperglycemia, said method comprising implanting into the subject an immunoisolatory device comprising isolated human cells stably transfected with the recombinant expression vector of claim 5, wherein said isolated human cells produce endogenous furin.

11. A method of reducing weight in a subject, said method comprising implanting into the subject an immunoisolatory device comprising isolated human cells stably transfected with the recombinant expression vector of claim 5, wherein said isolated human cells produce endogenous furin.

* * * * *